(12) United States Patent
Fukae

(10) Patent No.: US 8,308,706 B2
(45) Date of Patent: Nov. 13, 2012

(54) DISPOSABLE DIAPER

(75) Inventor: Akinori Fukae, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 478 days.

(21) Appl. No.: 12/449,787

(22) PCT Filed: Feb. 28, 2008

(86) PCT No.: PCT/JP2008/053520
§ 371 (c)(1),
(2), (4) Date: Aug. 26, 2009

(87) PCT Pub. No.: WO2008/108270
PCT Pub. Date: Sep. 12, 2008

(65) Prior Publication Data
US 2010/0106123 A1 Apr. 29, 2010

(30) Foreign Application Priority Data

Feb. 28, 2007 (JP) .................. 2007-050823
Feb. 28, 2007 (JP) .................. 2007-050824

(51) Int. Cl.
*A61F 13/15* (2006.01)
(52) U.S. Cl. ............ 604/393; 604/385.27; 604/385.01
(58) Field of Classification Search .................. 604/367, 604/385.01, 385.03, 385.101, 385.16, 385.22, 604/385.24–385.27, 393
See application file for complete search history.

(56) References Cited

U.S. PATENT DOCUMENTS

2004/0243083 A1* 12/2004 Matsuda et al. ......... 604/385.01
2005/0148965 A1 7/2005 Richlen et al.
2005/0177124 A1 8/2005 Kondo

FOREIGN PATENT DOCUMENTS

| JP | 2001-187086 | 7/2001 |
| JP | 2004-298362 | 10/2004 |
| JP | 2005-27839 | 2/2005 |
| JP | 2006-280581 | 10/2006 |
| WO | WO 2005/051264 | 6/2005 |

* cited by examiner

*Primary Examiner* — Michele M Kidwell
(74) *Attorney, Agent, or Firm* — DLA Piper LLP (US)

(57) ABSTRACT

In a disposable diaper, a ventral-side outer sheet and a back-side outer sheet are separated at a crotch portion, the back-side outer sheet has a main unit section that corresponds to joined sections in an up-down direction and a back-side extension section that extends below the back-side main unit section, the ventral-side outer sheet is composed of only a ventral-side main unit section that corresponds to the joined sections in the up-down direction, the back-side extension section has a central portion in the width direction overlapping the absorber and hip cover portions extending on both sides of the central portion in the back-side main unit section.

10 Claims, 18 Drawing Sheets

(a)

(b)

(a)

(b)

the present invention to solve the foregoing problem is as follows:

DISPOSABLE DIAPER

TECHNICAL FIELD

The present invention relates to underpants type disposable diapers in which an outer sheet is separated into two portions on a ventral side and a back side.

BACKGROUND ART

A general underpants type disposable diaper has front and back parts joined on both sides to thereby form joined sections on the both sides. The disposable diaper also includes an outer sheet with a waist opening and a pair of right and left leg openings, and includes an absorber that is fixed in an area of an inner surface ranging from a ventral side through a crotch portion to a back side along a central portion in the width direction. The disposable diaper can be worn by inserting both legs of a wearer through the waist opening into the leg openings.

Other than such a diaper with a single-piece outer sheet, there has been proposed a two-separated type disposable diaper which has ventral and back outer sheets (refer to Patent Document 1, for example). The two-separated disposable diaper has advantages that, at the time of manufacture, trims (unnecessary waste portions) can be reduced in punching out the leg openings, and materials for the ventral- and back-side outer sheets can be separately selected.

Meanwhile, the two-separated type can eliminate trims completely, but in this case, has no portions for covering both sides of the hip of a wearer, and thus may deteriorate in outer appearance and fit property. Therefore, the back-side outer sheet is provided with a back-side extension section having a central portion overlapping the absorber and hip cover portions extending on the both sides of the central portion, below the back-side main unit section corresponding to the joined sections in the up-down direction.

The hip cover portions in the back-side extension section may swell or curl or deteriorate in appearance. Therefore, there has been developed a diaper in which elongated resilient and elastic members such as rubber threads are fixed to the hip cover portions, in a state of being extended in the width direction at a predetermined extension ratio.

Patent Document 1: JP 2005-027839A

DISCLOSURE OF THE INVENTION

Technical Problems to be Solved

However, swelling and curling of the hip cover portions (hereinafter also referred simply to as a fit property) cannot be eliminated only by fixing elongated resilient and elastic members such as rubber threads in an extended state to the hip cover portions.

Therefore, a principal object of the present invention is to improve a fit property at the hip cover portions.

Means to Solve the Problems

The present invention to solve the foregoing problem is as follows:

<Invention According to Claim 1>

An underpants type disposable diaper, comprising:

a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction; and an absorber that is connected at a front end portion to the ventral-side outer sheet on an inner surface at a central portion in the width direction and is connected at a back end portion to the back-side outer sheet on an inner surface at a central portion in the width direction, and covers the back side through crotch portion to the ventral side, the ventral-side outer sheet and the back-side outer sheet being not connected but separated at the crotch portion, wherein the back-side outer sheet has a back-side main unit section that corresponds to the joined sections in an up-down direction, and a back-side extension section that extends below the back-side main unit section, the back-side extension section has a central portion in the width direction overlapping the absorber and hip cover portions extending on both sides of the central portion, in the back-side outer sheet, the back-side main unit section has an upper end portion, a lower end portion, and an intermediate portion between the two end portions in the up-down direction, a plurality of back-side waist elongated resilient and elastic members is fixed to the upper end portion, at intervals in the up-down direction and in a state of being extended in the width direction at a predetermined extension ratio; a plurality of first elongated resilient and elastic members is fixed to the intermediate portion and the lower end portion at least in areas not overlapping the absorber, at intervals in the up-down direction and in a state of being extended in the width direction at a predetermined extension ratio; and a plurality of second elongated resilient and elastic members is fixed to at least the hip cover portions in the back-side extension section, at intervals in the up-down direction and in a state of being extended in the width direction at a predetermined extension ratio, the ventral-side outer sheet is composed of only a ventral-side main unit section that corresponds to the joined sections in the up-down direction or is composed of a ventral-side main unit section that corresponds to the joined section in the up-down direction and a ventral-side extension section that extends below the ventral-side main unit section and has no resilient and elastic members, in the ventral-side outer sheet, the ventral-side main unit section has an upper end portion, a lower end portion, and an intermediate portion between the two end portions in the up-down direction, a plurality of ventral-side waist elongated resilient and elastic members is fixed to the upper end portion, at intervals in the up-down direction and in a state of being extended in the width direction at a predetermined extension ratio; a plurality of third elongated resilient and elastic members is fixed to the intermediate portion at least in areas not overlapping the absorber, at intervals in the up-down direction and in a state of being extended in the width direction at a predetermined extension ratio; and a plurality of fourth elongated resilient and elastic members is fixed to the lower end portion at least in areas not overlapping the absorber, at intervals in the up-down direction and in a state of being extended in the width direction at a predetermined extension ratio, and the back-side waist elongated resilient and elastic members, the ventral-side waist elongated and elastic members, the first elongated resilient and elastic members, the second elongated resilient and elastic members, the third elongated resilient and elastic members, and the fourth elongated resilient and elastic members, are each specified in number, fineness, extension ratio, interval, kind of a material, and arrangement pattern in the up-down direction, such that an inclination angle of the joined sections is found to be 20 degrees or less according to a joined section inclination test.

(Effect and Operation)

The inventors of the present invention have carried out earnest studies as to a fit property at the hip cover portions, and achieved findings from the studies described below. Specifically, conventional diapers exhibit a phenomenon in which the joined sections 12A between the back-side outer sheet 12B and the ventral-side outer sheet 12F are shifted in position toward the back side with increasing proximity to the lower ends, as shown in FIG. 9. This phenomenon causes swelling and curling of the hip cover portions.

The inventors have further proceeded with their studies and revealed that this phenomenon related closely to resilient and elastic properties of components of a diaper, and this phenomenon occurred mainly because contraction forces of elongated resilient and elastic members in the hip cover portions disrupted the balance of contraction forces between the ventral and back sides with the joined sections as boundaries therebetween, whereby the joined section is affected more strongly at the lower ends by contraction forces toward the back side.

The first invention has been accomplished on the basis of the foregoing findings, and is characterized in that the elongated resilient and elastic members are specified in number, fineness, extension ratio, interval, kind of a material, and arrangement pattern in the up-down direction, so that the inclination angle of the joined sections is found to be 20 degree or less according to a joined section inclination test. With such an arrangement, it is possible to prevent effectively curling or swelling of the hip cover portions while retaining the advantages of the two-separated type diaper.

According to a joined section inclination test, the inclination angle of the joined sections is measured in a manner as described below. First, as shown in FIG. 12(a), an absorber is removed from a disposable diaper to use the waist portion 12 alone as a specimen. The specimen 12 is folded along a central line of the ventral-side outer sheet 12F in the product width direction and a central line of the back-side outer sheet 12B in the product width direction, such that the folded parts of the ventral- and back-side sheets each overlap inside and reference end lines L1 of the both joined sections 12A (center-side end edges in the width direction of the joined sections 12A) overlap. Next, the folded specimen 12 is inserted into one chuck C1 of a tensile tester in an area ranging from one folding line toward the joined section by 10 mm entirely in the product up-down direction, and inserted into the other chuck C2 of the tensile tester in an area ranging from the other folding line toward the joined section by 10 mm entirely in the product front-back direction. Then, the tensile test is conducted entirely in the product up-down direction shown by arrows in the diagram. Subsequently, assuming that a distance between the chucks with the specimen 12 not stretched but naturally contracted (a naturally-contracted length) is designated as A and a distance between the chucks with the specimen 12 stretched until the resilient and elastic members produce no contraction anymore (a maximum stretched length) as B, a protractor is used to measure an inclination angle θ of a virtual line L2 connecting the upper and lower ends of the joined section reference end line L1 in the product up-down direction when the specimen is stretched until the distance between the chucks reaches (A+B)/2, as shown in FIG. 12(b), and the measured angle is set as a joined section inclination angle.

<Invention According to Claim 2>

The underpants type disposable diaper according to Claim 1, wherein a contraction force per one second elongated resilient and elastic member is equal to or weaker than a contraction force per one first elongated resilient and elastic member, and a contraction force per one fourth elongated resilient and elastic member is equal to or stronger than a contraction force per one third elongated resilient and elastic member.

(Effect and Operation)

In one preferred embodiment of the invention described in this claim, the inclination angle of the joined sections is found to be 20 degrees or less according to a joined section inclination test. By employing the arrangement described in this claim, the contraction forces of the elongated resilient and elastic members are well balanced in the around-waist direction, thereby suppressing movement of the lower parts of the joined sections toward the back side.

<Invention According to Claim 3>

The underpants type disposable diaper according to Claim 1 or 2, wherein contraction forces per constant width of the sections in the outer sheet meet a relationship: the lower end portion of the ventral-side main unit section≧the intermediate portion of the back-side main unit section>the intermediate portion of the ventral-side main unit section≧the lower end portion of the back-side main unit section and the back-side extension section.

(Effect and Operation)

In one preferred embodiment of the invention described in this claim, the inclination angle of the joined sections is found to be 20 degrees or less according to a joined section inclination test. With the arrangement described in this claim in particular, the contraction forces are more preferably balanced entirely in the up-down direction of the outer sheet.

<Invention According to Claim 4>

The underpants type disposable diaper according to any one of Claims 1 to 3, wherein the ventral-side outer sheet is composed of only a ventral-side main unit section, the back-side outer sheet and the ventral-side outer sheet are each formed by laminating two nonwoven fabrics with a basis weight of 10 to 30 g/m$^2$, a length of the lower end portion of the back-side main unit section and a length of the lower end portion of the ventral-side main unit section are equal and 30 to 100 mm in the up-down direction, the hip cover portions are 80 to 160 mm long in the width direction, and the hip cover portions are 30 to 80 mm long in the up-down direction, the first elongated resilient and elastic member in the lower end portion is 2 to 15 rubber threads made of synthetic rubber, 155 to 1,880 dtex in fineness and 200 to 350% in extension ratio, are arranged at intervals of 1 to 15 mm, the fourth elongated resilient and elastic members are 1 to 8 rubber threads made of synthetic rubber that are 155 to 1,880 dtex in fineness and 150 to 350% in extension ratio, and are arranged at intervals of 1 to 30 mm, and the second elongated resilient and elastic members are 2 to 10 rubber threads made of synthetic rubber that are 155 to 1,880 dtex in fineness and 150 to 300% in extension ratio, and are arranged at intervals of 5 to 40 mm.

(Effect and Operation)

In one preferred embodiment of the invention described in this claim, the inclination angle of the joined sections is found to be 20 degrees or less according to a joined section inclination test. By employing the arrangement described in this claim, the contraction forces of the elongated resilient and elastic members are well balanced in the around-waist direction to suppress movement of the lower parts of the joined sections toward the back side.

<Invention According to Claim 5>

The underpants type disposable diaper according to Claim 4, wherein a length of the upper end portion of the back-side main unit section and a length of the upper end portion of the ventral-side main unit section are equal and 15 to 80 mm in the up-down direction, a length of the intermediate portion of the back-side main unit section and a length of the intermediate portion of the ventral-side main unit section are equal and 30 to 100 mm in the up-down direction, the back-side waist elongated resilient and elastic members and the ventral-side waist elongated resilient and elastic members are each 3 to 22 rubber threads that are made of synthetic rubber, 155 to 1,880 dtex in fineness and 150 to 400% in extension ratio, and are arranged at intervals of 4 to 12 mm, and the first elongated resilient and elastic members in the intermediate portion and the third elongated resilient and elastic members are each 3 to 15 rubber threads that are made of synthetic rubber, 155 to 1,880 dtex in fineness and 150 to 300% in extension ratio, and are arranged at intervals of 1 to 15 mm.

(Effect and Operation)

With the arrangement in this claim in particular, the contraction forces are further preferably balanced in the up-down direction of the entire joined sections.

<Invention According to Claim 6>

The underpants type disposable diaper according to any one of Claims 1 to 5, wherein the hip cover portions are shaped at outer edges in the width direction, in a straight line or curved line approaching the absorber with increasing proximity to the crotch portion, and contraction forces of the second elongated resilient and elastic members acting on the hip cover portions become weaker with increasing proximity to the lower ends of the hip cover portions.

(Effect and Operation)

In consideration of covering the hip of a wearer with an improved appearance, the hip cover portions are preferably shaped, at the outer edges in the width direction, in a straight line or curved line approaching the absorber with increasing proximity to the crotch portion. However, in a diaper in which the second elongated resilient and elastic members are configured such that contraction forces thereof act equally on the hip cover portions in the up-down direction, the hip cover portions become prone to be excessively contracted at the lower ends if the contraction forces are set to prevent the hip cover portions from being curled at the upper ends, and in contrast, the hip cover portions become prone to be curled at the upper ends if the contraction forces are set such that the hip cover portions are appropriately contracted at the lower ends. In addition, the hip cover portions become prone to be shifted toward the back side at the joined sections. On the other hand, the arrangement described in this claim can prevent the foregoing problems effectively.

<Invention According to Claim 7>

The underpants type disposable diaper according to any one of Claims 1 to 6, wherein in the back-side outer sheet, with reference to a portion corresponding to the lower ends of the joined sections in the up-down direction, the first elongated resilient and elastic members are not arranged in an area above the portion up to 5 mm, and the second elongated resilient and elastic members are not arranged in an area below the portion down to 10 mm.

(Effect and Operation)

By not arranging the first and second elongated resilient and elastic members in specific areas in the vicinities of the lower ends of the joined sections in the back-side outer sheet, the first and second elongated resilient and elastic members arranged in areas other than the specific areas can exert contraction forces on the hip cover portions so as to cause neither swelling nor curling.

<Invention According to Claim 8>

The underpants type disposable diaper according to Claim 7, wherein the second elongated resilient and elastic members are all equal in fineness, interval, and material, and become lower in extension ratio at a decrease rate of 1 to 30%/mm with increasing proximity to the lower ends of the hip cover portions, or the second elongated resilient and elastic members are all equal in extension ratio, interval, and material and become decreased in fineness at a decrease rate of 5 to 150 dtex/mm with increasing proximity to the lower ends of the hip cover portions.

(Effect and Operation)

If the contraction forces of the second elongated resilient and elastic members acting on the hip cover portions are made weaker with increasing proximity to the lower ends of the hip cover portions, too a small decrease rate of contraction forces may deteriorate the effect, and too a large decrease rate of contraction forces may produce the opposite effect. Therefore, the decrease rate preferably falls within the range described in this claim.

<Invention According to Claim 9>

An underpants type disposable diaper, comprising:

a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction; and an absorber that is connected at a front end portion to the ventral-side outer sheet on an inner surface at a central portion in the width direction and is connected at a back end portion to the back-side outer sheet on an inner surface at a central portion in the width direction, and covers the back side through crotch portion to the ventral side, the ventral-side outer sheet and the back-side outer sheet being not connected but separated at the crotch portion, wherein the back-side outer sheet has a back-side main unit section that corresponds to the joined sections in an up-down direction, and a back-side extension section that extends below the back-side main unit section, the back-side extension section has a central portion in the width direction overlapping the absorber and hip cover portions extending on both sides of the central portion, the back-side main unit section has an upper end portion and a lower portion below the upper end portion in the up-down direction, back-side waist elongated resilient and elastic members are fixed to the upper end portion, in a state of being extended in the width direction at a predetermined extension ratio; a plurality of first elongated resilient and elastic members is fixed to the lower portion at least in areas not overlapping the absorber, at intervals in the up-down direction and in a state of being extended in the width direction at a predetermined extension ratio; and a plurality of second elongated resilient and elastic members is fixed to at least the hip cover portions, at intervals in the up-down direction and in a state of being extended in the width direction at a predetermined extension ratio, the ventral-side outer sheet is composed of only a ventral-side main unit section that corresponds to the joined sections in the up-down direction or is composed of a ventral-side main unit section that corresponds to the joined sections in the up-down direction and a ventral-side extension section that extends below the ventral-side main unit section and has no resilient and elastic members, in the ventral-side outer sheet, the ventral-side main unit section has an upper end portion in the up-down direction and a lower portion below the upper end portion, a plurality of ventral-side waist elongated resilient and elastic members is fixed to the upper end portion, at intervals in the up-down direction and in a state of being extended in the width direction at a predetermined extension ratio; and a plurality of third elongated resilient and elastic members is fixed to the lower portion at least in an area not overlapping the absorber, at intervals in the up-down direction and in a state of being extended in the width direction at a predetermined extension ratio, and in the back-side outer sheet, with reference to a portion corresponding to the lower ends of the joined sections in the up-down direction, the first elongated resilient and elastic members are not arranged in an area above the portion up to 5 mm, and the second elongated resilient and elastic members are not arranged in an area below the portion down to 10 mm.

(Effect and Operation)

The inventors of the present invention have conducted earnest studies and found that a fit property of the hip cover portions could be further improved by making adjustments to elongated resilient and elastic members in arrangement pattern and individual tensions at the hip cover portions and the vicinities thereof. Specifically, this is because, if, with reference to a portion corresponding to the lower ends of the joined sections in the up-down direction, the first elongated resilient and elastic members were provided in an area above the portion up to 5 mm or the second elongated resilient and elastic members were provided in an area below the portion down to 10 mm, the contraction forces of the first and second elongated resilient and elastic members provided in areas other than the foregoing areas would act on the hip cover portions so as to cause swelling or curling, through the first and second elongated resilient and elastic members arranged in the foregoing areas.

The second invention has been accomplished on the basis of the foregoing findings, and is characterized in that, with reference to the portion corresponding to the lower ends of the joined sections in the up-down direction, the first elongated resilient and elastic members are not arranged in an area above the portion up to 5 mm, and the second elongated resilient and elastic members are not arranged in the area above the portion down to 10 mm. As above, by not providing the first and second elongated resilient and elastic members in the specific areas in the vicinities of the lower ends of the joined sections in the back-side outer sheet, the first and second elongated resilient and elastic members can exert contraction forces on the hip cover portions so as to cause neither swelling nor curling.

<Invention According to Claim 10>

The underpants type disposable diaper according to Claim 9, wherein the ventral-side outer sheet is composed of only the ventral-side main unit section, the back-side outer sheet and the ventral-side outer sheet are each formed by laminating two nonwoven fabrics with a basis weight of 10 to 30 g/m$^2$, a length of the lower portion of the back-side main unit section and a length of the lower portion of the ventral-side main unit section are equal and 35 to 220 mm in the up-down direction, the hip cover portions are 80 to 160 mm long in the width direction, and the hip cover portions are 30 to 80 mm long in the up-down direction, the first elongated resilient and elastic members are 5 to 30 rubber threads that are made of synthetic rubber, 155 to 1,880 dtex in fineness and 200 to 350% in extension ratio, and are arranged at intervals of 1 to 15 mm, the second elongated resilient and elastic members are 2 to 10 rubber threads that are made of synthetic rubber, 155 to 1,880 dtex in fineness and 150 to 300% in extension ratio, and are arranged at intervals of 5 to 40 mm, the third elongated resilient and elastic members are 4 to 30 rubber threads that are made of synthetic rubber, 155 to 1,880 dtex in fineness and 150 to 300% in extension ratio, and are arranged at intervals of 3 to 8 mm, a length of the upper end portion of the back-side main unit section and a length of the upper end portion of the ventral-side main unit section are equal and 15 to 80 mm in the up-down direction, and the back-side waist elongated resilient and elastic members and the ventral-side elongated resilient and elastic members are each 3 to 22 rubber threads that are made of synthetic rubber, 155 to 1,880 dtex in fineness and 150 to 400% in extension ratio, and are arranged at intervals of 4 to 12 mm.

(Effect and Operation)

The second invention produces prominent effects in particular by employing the dimensions of the components and the arrangements of the elongated resilient and elastic members described in this claim.

Effect of the Invention

As stated above, the present invention brings about advantages such as an improved fit property of the hip cover portions.

BEST MODE FOR CARRYING OUT THE INVENTION

Embodiments of the present invention will be further described in detail below with reference to the drawings.

First Embodiment

FIGS. 1 to 5 show one example of an underpants type disposable diaper according to a first invention. In FIG. 1, the term "front-back direction" refers to a direction that links the ventral side to the back side; the term "width direction" a direction orthogonal to the front-back direction; and the term "up-down direction" a direction orthogonal to an around-waist direction, in other words, a direction that links a waist opening WO to a crotch portion.

The underpants type disposable diaper 10 has a ventral-side outer sheet 12F that covers a ventral side of a waist of a wearer, and a back-side outer sheet 12B that covers a back side of the waist of the wearer. The ventral-side outer sheet 12F and the back-side outer sheet 12B are joined together at joined sections 12A at edges on both sides in the width direction by heat sealing, ultrasonic welding or the like, thereby forming a barrel-shaped waist portion 12. As illustrated, if the ventral-side outer sheet 12B extends below the joined sections 12A, it is possible to provide an extension welding section that is integrally processed by heat sealing or the like in an area containing an extending portion in the up-down direction. By providing the extension welding section, it is possible to prevent that second elongated resilient and elastic members 16 are drawn in an extension section 14 described later. In a general joint pattern, the joined sections 12A each include a series of small welding points for a lower proportion of a welded area, in consideration of easiness to tear off the diaper on the both sides. However, since there is no need to consider easiness to tear for the extension welding section, the proportion of a welding area may be made higher at the extension welding section than at the joined sections 12A, so that the second elongated resilient and elastic members 16 can be welded and fixed in a reliable manner. Alternatively, the extension welding section may be welded in a curved line at edges of hip cover portions 14C to thereby prevent the second elongated resilient and elastic members 16 from being drawn in the hip cover portions 14C.

In addition, in the waist portion 12, the absorber 20 is connected at a front end portion to the ventral-side outer sheet 12F on an inner surface at a central portion in the width direction, and is connected at a back end portion to the back-side outer sheet 12B on an inner surface at a central portion in the width direction. The ventral-side outer sheet 12F and the back-side outer sheet 12B are not connected but separated at the crotch portion. A separated distance Y may be about 150 to 250 mm.

As seen from FIGS. 4 and 5, an upper opening at the waist portion 12 constitutes the waist opening WO through which the waist of a wearer passes, and sections surrounded by a lower edge of the waist portion 12 and side edges of the absorber 20 on the both sides in the width direction of the absorber 20 constitute leg openings LO through which the legs of a wearer pass. The diaper has the shape of a sand clock in the state of being torn off and opened at the joined sections 12A as shown in FIG. 1. The absorber 20 extends and covers from the back side through the crotch portion to the ventral side, and is intended to receive excreted objects, and absorb and retain body liquids. The waist portion 12 is designed to hold the absorber 20 with respect to a wearer.

(Outer Sheet)

The ventral-side outer sheet 12F and the back-side outer sheet 12B are formed by laminating two sheets S1 and S2 of a nonwoven fabric or the like, and those sheets have elongated resilient and elastic members 15 to 18, 19T, and 19U of rubber threads or the like between the two sheets S1 and S2 at a predetermined extension ratio for an increased fit to the waist of a wearer, as shown in FIG. 3. If a nonwoven fabric is used, a preferred basis weight thereof is about 10 to 30 g/m². In addition, there is no particular limitation on raw fibers for use in such a nonwoven fabric. For example, the raw fibers may be any of synthetic fibers based on olefin such as polyethylene or polypropylene, polyester, polyamide or the like, recycled fibers such as rayon or cupra, natural fibers such as cotton, mixed or composite fibers of two or more of the foregoing fibers. Further, the nonwoven fabric may be produced by any processing method. For example, such a processing method may be any known method such as a spun lace method, spun bonding method, thermal bonding method, melt-blown method, needle punching method, air-through method, point bonding method. In addition, the elongated resilient and elastic members 15 to 18, 19T, and 19U may use synthetic rubber or natural rubber.

In addition, characteristically, the elongated resilient and elastic members are specified in number, fineness, extension ratio, interval, kind of a material, and arrangement pattern, in such a manner that the outer sheet 12 is well balanced in contraction force in the width direction between the ventral and back sides with the joined sections as boundaries, and that an inclination angle of the joined sections is found to be 20 degrees or less, preferably 10 degrees or less, more preferably 5 degree or less according to a joined section inclination test.

More specifically, the back-side outer sheet 12B has a back-side main unit section 13 that corresponds to the joined sections 12A in the up-down direction, and the back-side extension section 14 that extends below the back-side main unit section 13. The back-side extension section 14 has a central portion 14M in the width direction that overlaps the absorber 20 and the hip cover portions 14C that extend on both sides of the central portion 14M.

The back-side extension section 14 can be formed in an arbitrary shape. In an illustrated example, the back-side extension section 14 extends at an upper end portion below the back-side main unit section 13, with the same width as the main unit section 13, and the back-side extension section 14 is made narrower on a lower side with increasing proximity to the crotch portion. The back-side extension section 14 may be omitted at a section with the same width as the back-side main unit section 13. With such an arrangement, outer edges 14e of the hip cover portions 14C in the width direction each form a straight or curved line approaching toward the absorber 20 with increasing proximity to the crotch portion, whereby the hip cover portions 14C are shaped so as to cover the hip of a wearer in an easy manner. Dimensions of the back-side extension section 14 can be decided as appropriate. More preferably, the hip cover portions 14C each have a length 14x of 80 to 160 mm in the width direction (a maximum separated distance in the width direction between the outer edge 14e of the hip cover portion 14C and side edge of the absorber 20 in the width direction), and the hip cover portions 14C each have a length Ply of 30 to 80 mm in the up-down direction (an extension length). In addition, assuming that an area of a square defined by a widest portion of the back-side extension section 14 in the width direction and a widest portion of the back-side extension section 14 in the up-down direction is designated as S, the area of the back-side extension section 14 is preferably about 20 to 80% of S, more preferably about 40 to 60% of S, which makes the hip portion excellent in appearance and fit property.

The back-side main unit section 13 is conceptually divided in the up-down direction into an upper end portion (waist portion) W, a lower end portion U, and an intermediate portion M between the upper and lower end portions. Although dimensions of those portions vary depending on the size of the diaper, the upper end portion W may be 15 to 80 mm long in the up-down direction, the lower portion U 30 to 100 mm long in the up-down direction, and the intermediate portion M 30 to 100 mm long in the up-down direction. If no clear boundary can be fixed between the upper end portion W and the intermediate portion M or between the intermediate portion M and the lower end portion U (i.e. if those portions cannot be clearly divided by the elongated resilient and elastic members' fineness, extension ratio, interval, kind of a material, arrangement pattern in the up-down or width direction, or the like), the lower end portion Z is the same as the upper end portion W in length in the up-down direction, and the upper end portion W ranges from the upper end down to 30 mm.

A plurality of back-side waist resilient and elastic members 17 is continuously fixed to the upper end portion (waist portion) W of the back-side main unit section 13 in the entire width direction, at intervals in the up-down direction and in a state of being extended in the width direction at a predetermined extension ratio. In addition, out of the back-side waist resilient and elastic members 17, one or more arranged in a section adjacent to the intermediate portion M of the backside main unit section 13 may overlap the absorber 20. As the back-side waist resilient and elastic members 17, about 3 to 22 rubber threads with a fineness of about 155 to 1,880 dtex, in particular about 470 to 1,240 dtex (in the case of synthetic rubber. For natural rubber, about 0.05 to 1.5 mm$^2$, particularly about 0.1 to 1.0 mm$^2$, in cross-section area) are preferably fixed at intervals of 4 to 12 mm at an extension ratio of about 150 to 400%, in particular about 220 to 320%. In addition, the back-side waist resilient and elastic members 17 do not need to be all the same in fineness and extension ratio, and may be different in fineness and extension ratio between the upper and lower sides of the waist portion, for example.

In addition, in the intermediate portion M and the lower end portion U of the back-side main unit section 13 except for the central portion in the width direction that overlaps the absorber 20, a plurality of first elongated resilient and elastic members 15 is continuously fixed in the entire width direction to areas above and on both sides of the central portion in the width direction overlapping the absorber 20, at intervals in the up-down direction and in a state of being extended in the width direction at a predetermined extension ratio. The first elongated resilient and elastic members 15 may be partly arranged in the back-side main unit section 13 in the up-down direction, but are preferably arranged in the substantially entire back-side main unit section 13 (where elastic forces of the members acts entirely).

The first elongated resilient and elastic members 15 preferably use rubber threads with a fineness of about 155 to 1,880 dtex, particularly about 470 to 1,240 dtex (in the case of synthetic rubber. For natural rubber, about 0.05 to 1.5 mm$^2$, particularly about 0.1 to 1.0 mm$^2$, in cross-section area). In addition, preferably, about 3 to 15 first elongated resilient and elastic members 15 are arranged in the intermediate portion M at intervals of 1 to 15 mm, at an extension ratio of about 150 to 300%, particularly about 220 to 280%, and about 2 to 15 first elongated resilient and elastic members 15 are arranged in the lower end portion U at intervals of 1 to 15 mm at an extension ratio of about 200 to 350%, particularly about 240 to 300%.

Further, in the back-side extension section 14 except for the central portion in the width direction that overlaps the absorber 20, a plurality of second elongated resilient and elastic members 16 is continuously fixed in the entire width direction to areas on the both sides of the central portion overlapping the absorber 20 (at least covering the entire hip cover portions 14C), at intervals in the up-down direction and in a state of being extended in the width direction at a predetermined extension ratio. The second elongated resilient and elastic members 16 may be partly arranged in the back-side extension section 14 in the up-down direction, but are preferably arranged in the substantially entire back-side extension section 14 (where elastic forces of the members acts entirely).

As the second elongated resilient and elastic members 16, about 2 to 10 rubber threads with a fineness of about 155 to 1,880 dtex, particularly about 470 to 1,240 dtex (in the case of synthetic rubber. For natural rubber, about 0.05 to 1.5 mm$^2$, particularly about 0.1 to 1.0 mm$^2$, in cross-section area) are preferably fixed at intervals of 5 to 40 mm, in particular 5 to 20 mm, at an extension ratio of 150 to 300%, in particular 180 to 260%. In particular, a contraction force per one second elongated resilient and elastic member 16 is preferably equal to or weaker than a contraction force per one first elongated resilient and elastic member 15. Specifically, the fineness of the second elongated resilient and elastic members 16 may be made equal to or lower than the fineness of the first elongated resilient and elastic members 15, and the extension ratio of the second elongated resilient and elastic members 16 may be made lower than the extension ratio of the first elongated and resilient and elastic members 15. In contrast, the extension ratio of the second elongated resilient and elastic members 16 may be equal to or lower than the extension ratio of the first elongated resilient and elastic members 15, and the fineness of the second elongated resilient and elastic members 16 may be made lower than the fineness of the first elongated resilient and elastic members 15. Otherwise, those elongated resilient and elastic members can be different in contraction force by variations in number, interval, kind of a material, or arrangement pattern in the up-down direction.

In a particularly preferred arrangement, the contraction forces of the second elongated resilient and elastic members 16 become weaker with increasing proximity to the lower ends of the hip cover portions 14C. Specifically, the second elongated resilient and elastic members 16 closer to the lower ends of the hip cover portions 14C may be lowered in extension ratio, reduced in fineness, arranged at wider intervals, or use a material with weaker elastic forces, or may be configured in any combination of the foregoing methods. If the second elongated resilient and elastic members 16 are decreased in extension ratio with identical fineness, interval, and material, a range of decrease (for each position change of 1 mm in the up-down direction) may be from about 1 to 30%/mm for example, preferably from about 1 to 10%/mm. If the second elongated resilient and elastic members 16 are decreased in fineness with identical extension ratio, interval, and material, a range of decrease (for each position change of 1 mm in the up-down direction) may be from about 5 to 150 dtex/mm for example, preferably from about 5 to 50 dtex/mm.

Meanwhile, the ventral-side outer sheet 12F is preferably composed of only the ventral-side main unit section (corresponding to the joined sections 12A in the up-down direction), basically in a manner similar to the back-side main unit section 13 of the back-side outer sheet 12B. Therefore, the ventral-side outer sheet 12F takes the shape of a rectangle extending along the waist portion and has no extension section unlike the back-side outer sheet 12B having the back-side extension section 14. Accordingly, an upper end portion, intermediate portion and lower end portion in the up-down direction have the same reference numerals W, M, and U, respectively, as those of the back-side outer sheet 12B. The upper end portion W, intermediate portion M, and lower end portion U of the ventral-side outer sheet 12F are preferably equal in length in the up-down direction as those of the back-side outer sheet 12B, but may be different to such an extent that the balance of contraction forces in the present invention can be achieved. If no boundary can be clearly fixed between the intermediate portion M and the lower end portion Z to define the lower portion U (the intermediate portion M and the lower end portion Z are not clearly divided by the elongated resilient and elastic members' fineness, extension ratio, interval, kind of a material, or arrangement pattern in the up-down direction or width direction), the lower end portion Z is the same as the upper end portion W in length in the up-down direction, and the upper end portion W ranges from the upper end down to 30 mm.

Specifically, a plurality of ventral-side waist resilient and elastic members 18 is continuously fixed in the entire width direction to the upper end portion (waist portion) W of the ventral-side outer sheet (ventral-side main unit section) 12F, at intervals in the up-down direction and in a state of being extended in the width direction at a predetermined extension ratio. The ventral-side waist resilient and elastic members 18 in the ventral-side outer sheet 12F are preferably approximated as much as possible to the back-side waist resilient and elastic members 17 in the back-side outer sheet 12B in number, fineness, extension ratio, interval, and arrangement pattern in the up-down direction, but may be different to such an extent that the balance of contraction forces in the present invention can be achieved. Specifically, a difference in number is 10 or less, preferably 5 or less; a difference in fineness is 1,880 dtex or less, preferably 470 dtex or less; a difference in extension ratio is 100% or less, preferably 40% or less; and a difference in interval is 10 mm or less, preferably 5 mm or less.

In addition, in the intermediate portion M of the ventral-side outer sheet (ventral-side main unit section) 12F except for a central portion in the width direction overlapping the absorber 20, a plurality of third elongated resilient and elastic members 19T is continuously fixed in the entire width direction to areas above and on both sides of the central portion, at intervals in the up-down direction and in a state of being extended in the width direction at a predetermined extension ratio. The third elongated resilient and elastic members 19T may be partly arranged in the intermediate portion M in the up-down direction, but are preferably arranged in the substantially entire intermediate portion M (where contraction forces entirely act).

The third elongated resilient and elastic members 19T are preferably approximated as much as possible to the first elongated resilient and elastic members 15 arranged in the intermediate portion M in number, fineness, extension ratio, interval, and arrangement pattern in the up-down direction, but may be different to such an extent that the balance of contraction forces in the present invention can be achieved. Specifically, a difference in number is 10 or less, preferably 5 or less; a difference in fineness 1,880 dtex or less, preferably 470 dtex or less; a difference in extension ratio 100% or less, preferably 40% or less; and a difference in interval 10 mm or less, preferably 5 mm or less.

Further, in the lower end portion U of the ventral-side outer sheet 12F (ventral-side main unit section) except for the central portion in the width direction overlapping the absorber 20, a plurality of fourth elongated resilient and elastic members 19U is continuously fixed in the entire width direction to areas above and on both sides of the central portion, at intervals in the up-down direction and in a state of being extended in the width direction at a predetermined extension ratio. The fourth elongated resilient and elastic members 19U may be partly arranged in the lower end portion U in the up-down direction, but are preferably arranged in the substantially entire lower end portion U (where contraction forces entirely act).

The fourth elongated resilient and elastic members 19U are preferably approximated as much as possible to the first elongated resilient and elastic members 15 arranged in the lower end portion U in number, interval, and arrangement pattern in the up-down direction, but may be different to such an extent that the balance of contraction forces in the present invention can be achieved. Specifically, a difference in number is 10 or less, preferably 5 or less; and a difference in interval is 10 mm or less, preferably 5 mm or less.

In addition, the fourth elongated resilient and elastic members 19U are preferably about 155 to 1,880 dtex, in particular preferably about 470 to 1,240 dtex in fineness (in the case of synthetic rubber. For natural rubber, about 0.05 to 1.5 $mm^2$, in particular about 0.1 to 1.0 $mm^2$ in cross-section area), and are about 150 to 350%, in particular preferably about 220 to 320% in extension ratio.

In particular, a contraction force per one fourth elongated resilient and elastic member 19U is preferably equal to or stronger than a contraction force per one third elongated resilient and elastic member 19T. Specifically, the fineness of the fourth elongated resilient and elastic members 19U may be equal to or higher than the fineness of the third elongated resilient and elastic members 18, and the extension ratio of the fourth elongated resilient and elastic members 19U may be made higher than the extension ratio of the third elongated resilient and elastic members 18. In contrast, the extension ratio of the fourth elongated resilient and elastic members 19U may be equal to or higher than the extension ratio of the third elongated resilient and elastic members 18, and the fineness of the fourth elongated resilient and elastic members 19U may be higher than the fineness of the third elongated resilient and elastic members 18. Otherwise, those elongated resilient and elastic members 19U may be made different in contraction force by variations in number, interval, kind of a material, or arrangement pattern in the up-down direction.

In the thus configured underpants type disposable diaper, while advantages of the two-separated type can be retained and curling and swelling of the hip cover portions 14C can be suppressed, the contraction forces of the elongated resilient and elastic members in the ventral-side outer sheet 12F and the contraction forces of the elongated resilient and elastic members in the back-side outer sheet 12B can be balanced with the joined sections 12A as boundaries therebetween, and an inclination angle θ1 of the joined sections can be kept at 20 degrees or less, as shown in FIG. 8. That is, the joined sections 12A become less prone to be shifted in position toward the back side with increasing proximity to the lower ends (refer to FIG. 9). As a result, it is possible to effectively prevent the hip cover portions 14C from curling up or swelling.

Particularly in this embodiment, when compared by contraction force per constant width, contraction forces of the sections of the outer sheet 12 preferably meet a relationship: the lower end portion of the ventral-side main unit section≧the intermediate portion of the back-side main unit section>the intermediate portion of the ventral-side main unit section≧the lower end portion of the back-side main unit section and the back-side extension section. Contraction forces of the sections of the outer sheet 12 can be adjusted by appropriately setting the first, second, third, and fourth elongated resilient and elastic members 15, 16, 19T, and 19U in fineness, extension ratio, number, interval, kind of a material, or arrangement pattern in the up-down direction. In addition, the matter that the intermediate portion of the ventral-side main unit section is stronger in contraction force than the lower end portion of the back-side main unit section and the back-side extension section, indicates here that the contraction forces of the intermediate portion of the ventral-side main unit section are stronger than both of the contraction forces of the lower end portion of the back-side main unit section and the contraction forces of the back-side extension section, not that the contraction forces of the intermediate portion of the ventral-side main unit section are stronger than an average of the contraction forces of the lower end portion of the back-side main unit section and the contraction forces of the back-side extension section.

A contraction force per constant width refers to a stress applied to a sheet per constant width (in the up-down direction) when the sheet is stretched in the product width direction (a contraction force per unit width in the up-down direction), and is measured in such a manner as described below. First, a portion to be measured is cut out from the outer sheet 12 to prepare a specimen. The specimen is inserted at one end in the product width direction into one chuck C1 of a tensile tester, and inserted at the other end into the other chuck C2 of the same, and then the specimen is subjected to a tension test.

Assuming that a distance between the chucks with the specimen not stretched but naturally contracted (a naturally-contracted length) is designated as A and a distance between the chucks with the specimen stretched until the resilient and elastic members exert no contraction anymore (a maximum stretched length) is designated as B, a stress applied to between the chucks is measured when the specimen is stretched such that a distance between the chucks reaches (A+B)/2. Then, the stress is divided by the width of the specimen in the up-down direction, and the resultant is set as a contraction force (N/10 mm). For example, the contraction force of the back-side extension section 14 is determined by measuring a stress on the entire back-side extension section 14 as a specimen by the foregoing method, and dividing the stress by the width of the back-side extension section 14 in the up-down direction. Even if the back-side extension section 14 partly includes the second elongated resilient and elastic members 16, the contraction force of the back-side extension section 14 is determined by the method described above.

Meanwhile, in an arrangement with the first and second elongated resilient and elastic members 15 and 16 on the both sides in the width direction except for the central portion in the width direction that overlaps the absorber 20, as shown in the diagram, the resilient and elastic members may exist only on the both sides in the width direction. Alternatively, in such an arrangement, the resilient and elastic members may straddle the absorber 20 in the width direction from one to the other sides of the absorber 20, and be cut off at the central portion in the width direction that overlaps the absorber 20 so as to exert no elastic force (this is virtually equal to no provision of the resilient and elastic members). Further, in the present invention, the first and second elongated resilient and elastic members 15 and 16 may also straddle the absorber 20 in the width direction from one to the other sides of the absorber 20 so that elastic force can act entirely in the width direction on the back-side main unit section 13 and the back-side extension section 14.

The second elongated resilient and elastic members 16 are not welded at the joined sections 12A on the side edges to the sheets, unlike the first elongated resilient and elastic members 15. Accordingly, in particular when making the second elongated resilient and elastic members 16 higher in extension ratio than the first elongated resilient and elastic members 15 as in the invention of the subject application, the second elongated resilient and elastic members 16 are preferably subjected to some process for prevention of a drawn-in phenomenon. As described above, in a preferred means, an extension welding section may be provided so as to extend from the joined sections 12A. Otherwise, the second elongated resilient and elastic members 16 and the sheets S1, S2 may be adhered to each other with an increased strength by another method. For this end, an adhesive can be applied directly to the second elongated resilient and elastic members 16 for an increased adhesive strength, for example. However, using a large amount of adhesive may deteriorate resilient and elastic areas in texture, and therefore the members and sheets are desirably fixed by welding as described below.

Moreover, in an arrangement in which the second elongated resilient and elastic members 16 are cut off at the central portion in the width direction overlapping the absorber 20 for elimination of an elastic force, as described above, the second elongated resilient and elastic members 16 are preferably subjected at the ends of the central portion in the width direction to a similar process for prevention of a drawn-in phenomenon. When welding and fixing the second elongated resilient and elastic members 16 at the ends to the nonwoven fabrics S1, S2, for example, the second elongated resilient and elastic members 16 may be welded in approximately straight welding lines arranged so as to traverse longitudinally the second elongated resilient and elastic members 16 arranged in the width direction. Those drawn-in prevention measures may be combined.

(Method for Fixing the Resilient and Elastic Members by Welding)

FIG. 6 shows a method for fixing the second elongated resilient and elastic members 16 by a force of friction with sheets S1, S2 constituting the ventral-side outer sheet 12F and/or the back-side outer sheet 12B. In the method, the sheets S1, S2 are welded at predetermined intervals in the vicinities of the both ends of the second elongated resilient and elastic members 16 in the width direction, while the second elongated resilient and elastic members 16 are in a state of being stretched. In the diagram, reference character M denotes a welded portion, and reference character N a non-welded portion. With such an arrangement, the second elongated resilient and elastic members 16 can be firmly fixed without the use of an adhesive. In addition, since the second elongated resilient and elastic members 16 are not adhered, resilient and elastic areas can be provided with air permeability and softness. The welding may be ultrasonic welding or thermal welding. However, ultrasonic welding is more preferred because around the second elongated resilient and elastic members 16 and the sheets S1, S2, affection of heat and pressure is smaller in ultrasonic welding than thermal welding.

FIG. 7 shows a method for fixing the second elongated resilient and elastic members 16 to the sheets S1, S2 by a force of friction with the sheets S1, S2 and a force of adhesion at the ends of the second elongated resilient and elastic members 16 in the width direction. In the method, while the both ends of the second elongated resilient and elastic members 16 in the width direction are in a state of being stretched, the second elongated resilient and elastic members 16 and the sheets S1, S2 are welded together at predetermined intervals. In the diagram, reference character M denotes a welded portion, and reference character N a non-welded portion. With such an arrangement, the second elongated resilient and elastic members 16 can be more firmly fixed by a force of friction with the sheets S1, S2 and a force of adhesion at the ends of the second elongated resilient and elastic members 16 in the width direction. Since the second elongated resilient and elastic members 16 are adhered only at the ends in the width direction, there is no fear that the second elongated resilient and elastic members 16 are deteriorated or cut off.

The second elongated resilient and elastic members 16 are fixed to the sheets S1, S2 by a force of friction with the sheets S1, S2 in such a manner that the second elongated resilient and elastic members 16 are intermittently welded in a state of being stretched at inner and outer layers near the both ends in the width direction, whereby the second elongated resilient and elastic members 16 are fixed to the sheets S1, S2. Accordingly, by removing load afterward (no tension), the second elongated resilient and elastic members 16 are increased in cross-section outer diameter, and a pressing force is applied to the second elongated resilient and elastic members 16 so as to be sandwiched in the sheets S1, S2 at the welded portions on the both sides in the width direction. Therefore, the second elongated resilient and elastic members 16 do not need to be fixed with an adhesive, and the second elongated resilient and elastic members 16 can be fixed to the sheets S1, S2 only by a force of friction with the sheets S1, S2.

(Absorber)

The absorber 20 may take any shape, and is of a rectangle in the illustrated arrangement. As shown in FIG. 2, the absorber 20 includes a top sheet 30 formed of a nonwoven fabric, for example, that lets a liquid pass through, and an absorbent element 50, in this order from a usage side. In general, a liquid impervious sheet 70 formed of a plastic sheet or the like is provided on the underside of the absorbent element 50. A crotch outer sheet 12M may be fixed to the underside of the liquid impervious sheet 70 so as to cover the entire underside of the absorber 20 or cover an entire portion of the absorber 20 exposed between the ventral-side outer sheet 12F and the back-side outer sheet 12B. The crotch outer sheet 12M may use the same material as that for the ventral-side outer sheet 12F and the back-side outer sheet 12B, or may use a different material. In addition, to transfer a liquid having passed through the top sheet 30 quickly to the absorbent element 50, an intermediate sheet (second sheet) 40 may be interposed between the top sheet 30 and the absorbent element 50. Further, to prevent leakage of an excreted object to the both sides of the absorber 20, barrier cuffs 60, 60 may be erected on the both sides of the absorber 20. Although not shown, constituent members of the absorber 20 can be fixed to each other by solid, bead or spiral application of a hot-melt adhesive or the like.

The absorber 20 may be detachably connected to the outer sheet 20 using mechanical fasteners or adhesive materials.
(Top Sheet)

The top sheet 30 has a liquid pervious property. Therefore, a material for the top sheet 30 only needs to have liquid perviousness, and may be a porous or nonporous nonwoven fabric or a porous plastic sheet, for example. In addition, there is no particular limitation on raw fibers for use in such a nonwoven fabric. For example, the raw fibers may be any of synthetic fibers based on olefin such as polyethylene or polypropylene, polyester, polyamide or the like, recycled fibers such as rayon or cupra, natural fibers such as cotton, mixed or composite fibers of two or more of the foregoing fibers. Further, the nonwoven fabric may be produced by any processing method. For example, the processing method may be any known method such as a spun lace method, spun bonding method, thermal bonding method, melt-blown method, needle punching method, air-through method, point bonding method. For example, if flexibility and drape property are needed, the spun bonding method or the spun lace method is preferred. If high bulk and softness are required, the air-through method, the point bonding method, or the thermal bonding method is preferred.

In addition, the top sheet 30 may be a single sheet or a laminated sheet obtained by sticking two or more sheets to each other. Similarly, the top sheet 30 may be a single sheet or two or more sheets in a planar direction.
(Interlayer Sheet)

To rapidly move a fluid having passed through the top sheet 30 to the absorbent body, an interlayer sheet 40 may be provided, which is generally called "second sheet" and higher in fluid permeability rate than the top sheet 30. The interlayer sheet 40 allows a fluid to move quickly to the absorbent body to thereby enhance an absorption performance of the absorbent body. The interlayer sheet 40 also prevents a "backflow" phenomenon in which a fluid flows back from the absorbent body to thereby keep the top sheet 30 in a dry condition. The interlayer sheet 40 may be omitted.

The interlayer sheet 40 may use the same material as that of the top sheet 30, or may use a spun lace, a pulp nonwoven fabric, a mixed sheet of pulp and rayon, point-bonded or crepe paper, for example. In particular, an air-through nonwoven fabric or a spun-bonded nonwoven fabric is preferred.

Although in the illustrated embodiment, the interlayer sheet 40 is made shorter in width than the absorbent body 56 and is centered with respect to the absorbent body 56, the interlayer sheet 40 may also be provided across a full width of the absorbent body 56. A length of the interlayer sheet 40 in the longitudinal direction may be the same as that of the absorbent body 56, or may be in a shorter range centered in an area for receiving a fluid. A typical material for the interlayer sheet 40 is a highly liquid pervious nonwoven fabric.
(Liquid Impervious Sheet)

The liquid impervious sheet 70 simply refers to a sheet provided on an underside of the absorbent body 56. The absorbent body 56 is interposed between the liquid impervious sheet 70 and the top sheet 30 in this embodiment. There is thus no particular limitation on a material for the liquid impervious sheet 70. Specifically, the material may be any of olefin resins such as polyethylene and polypropylene, laminated nonwoven fabrics in which a nonwoven fabric is laminated on a polyethylene sheet or the like, and nonwoven fabrics to which a water-proof film is interposed for virtual liquid imperviousness (in this case, the water-proof film and the nonwoven fabric constitute a liquid impervious sheet), for example. As a matter of course, in addition to the foregoing examples, there are liquid impervious, moisture pervious sheets that have been favorably used in recent years from the viewpoint of prevention of stuffiness. Such a sheet made of a liquid impervious and moisture pervious material may be a microporous sheet obtained by melting and kneading an inorganic filling agent into an olefin resin such as polyethylene or polypropylene, to thereby form a sheet and then extending the sheet in a uniaxial or biaxial direction, for example. Further, the liquid impervious sheet 70 may use a sheet that is given liquid imperviousness without the use of a waterproof film, by using a nonwoven fabric of micro denier fibers, applying heat or pressure to make gaps in fibers smaller with enhanced leakage resistance, coating with high water-absorption resin or hydrophobic resin, or applying a water repellent agent.

The liquid impervious sheet 70 can be extended to the usage surface (not shown) so as to wrap around the sides to thereby prevent lateral leakage of a body fluid. In this embodiment, lateral leakage is prevented by interposing a second liquid impervious sheet 72 in the double barrier sheet 64 forming barrier cuffs 60. According to this embodiment, since the liquid impervious sheet 72 extends to erected portions of the barrier cuffs 60, it is possible to advantageously prevent lateral diffusion of a body fluid along the top sheet 30 and lateral leakage of loose stool between the barrier cuffs 60, 60.

The liquid impervious sheet may also have designed patterns prepared by printing or coloring on the inner or outer surface. In addition, the liquid impervious sheet may have a printed or colored design sheet attached to the outer surface, as a member different from the crotch outer sheet. Further, the liquid impervious sheet may include an indicator on the inner side to indicate voiding of urine by some visual change.
(Barrier Cuffs)

The barrier cuffs 60, 60 on the both sides of the product are designed to block and prevent urine or loose stool from moving and leaking laterally over the top sheet 30. The barrier cuffs 60, 60 are additional elements.

The illustrated barrier cuffs 60 are formed by laminating two water repellent nonwoven fabric sheets so as to cover from the underside of the absorbent body 56 to a downward folded portion of the top sheet 30, and project toward the upper side of the absorbent body 56. To block urine moving laterally over the top sheet 30, the second liquid impervious sheet 72 is interposed between the two nonwoven fabric sheets forming the barrier cuffs 60. Although not shown, the liquid impervious sheet 70 may be inserted at side portions into between the two nonwoven fabric sheets, and extended to midpoints in the barrier cuffs 60 projecting toward the upper side.

The barrier cuffs 60 can be designed in shape as appropriate. In the illustrated example, the resilient and elastic members, e.g., rubber threads 62 are fixed in an extended state at the leading ends and intermediate portions of projections in the barrier cuffs 60 so that the barrier cuffs 60 are erected by a stretching force of the rubber threads 62 when the diaper is being used. In this arrangement, the rubber threads 62 at the intermediate portions are located closer to a center of the top sheet 30 as compared with the rubber threads 62, 62 at the leading ends, and are fixed at front and back end portions of the top sheet 30, and therefore the barrier cuffs 60 are erected at base portions in such a manner as to be slant to the center, and are erected from the intermediate portions to the leading ends in such a manner as to be slant outward, as shown in FIG. 2.

(Absorbent Element)

The absorbent element 50 has the absorbent body 56, and an envelope sheet 58 that envelops at least an under surface and side surfaces of the absorbent body 56. The envelope sheet 58 may be omitted. Further, in the illustrated arrangement, a holding sheet 80 is disposed between the absorbent body 56 and the envelope sheet 58 on the underside (lower side). The holding sheet 80 may be omitted.

(Absorbent Body)

The absorbent body 56 may be an accumulation of short fibers of fluff pulp or the like, an assembly of filaments 52, 52 . . . , or others. The assembly of filaments 52, 52 . . . can be obtained by opening a tow (fiber bundle). Constitutional fibers for the tow may be any of polysaccharides or derivatives thereof (such as cellulose, cellulose ester, chitin, and chitosan), synthetic polymers (such as polyethylene, polypropylene, polyamide, polyester, polylactamide, and polyvinyl acetate) and the like, for example. In particular, cellulose ester or cellulose is preferred.

Usable celluloses include celluloses derived from plants such as cotton, linters and wood pulp, bacterial celluloses, and regenerated celluloses such as rayon. Regenerated celluloses may be in the form of spun fibers.

Preferably used cellulose esters include: organic acid esters such as cellulose acetate, cellulose butyrate, and cellulose propionate; mixed acid esters such as cellulose acetate propionate, cellulose acetate butyrate, cellulose acetate phthalate, and cellulose nitrate acetate; and cellulose ester derivatives such as polycaprolactone grafted cellulose ester, for example. These cellulose esters may be used singly or in combination. A viscosity average degree of polymerization of a cellulose ester is about 50 to 900 for example, preferably about 200 to 800. An average degree of substitution of a cellulose ester is about 1.5 to 3.0 (e.g. 2 to 3), for example.

An average degree of polymerization of a cellulose ester may be about 10 to 1,000 for example, preferably about 50 to 900, and more preferably about 200 to 800. An average degree of substitution of a cellulose ester may be about 1 to 3 for example, preferably about 1 to 2.15, and more preferably about 1.1 to 2.0. An average degree of substitution of a cellulose ester may be selected from a viewpoint of enhancing biodegradability.

Cellulose ester may be an organic acid ester (ester of organic acid with a carbon number of about 2 to 4, for example), and is preferably in particular a cellulose acetate. An acetylation degree of a cellulose acetate is about 43 to 62% in many cases, and preferably in particular about 30 to 50% with higher biodegradability. A particularly preferred cellulose ester is cellulose diacetate.

The tow constitutional fibers may contain various additives, for example, a heat stabilization agent, coloring agent, oil solution, retention aid, whiteness improving agent, and the like.

A fineness of the tow constitutional fibers is 1 to 16 deniers for example, preferably 1 to 10 deniers, and more preferably 1 to 6 deniers. The tow constitutional fibers may be non-crimped fibers, but preferably crimped fibers. A degree of crimping of the crimped fibers may be about 5 to 75 crimps per inch, preferably about 10 to 50 crimps per inch, and more preferably about 15 to 50 crimps per inch. In many cases, uniformly crimped fibers are used. By using such crimped fibers, it is possible to produce a high-integration tow due to fiber entanglement, and manufacture a high-bulk, lightweight absorbent body. There is no particular limitation on a cross-section shape of the tow constitutional fibers, and the tow constitutional fibers may be circular, elliptic, odd (e.g. Y, X, I, or R letter) or hollow in cross section, for example. The tow constitutional fibers can be used as a tow (fiber bundle) of about 1,000 to 1,000,000 single fibers for example, preferably about 2,000 to 1,000,000 single fibers. Such a fiber bundle is preferably formed by binding about 1,000 to 1,000,000 continuous fibers.

Bales of tow of cellulose diacetate preferably used in the present invention are made commercially available by Celanese Corp., Daicel Chemical Industries, Ltd., and others. A bale of tow of cellulose diacetate is about 0.5 g/cm$^3$ in density and 400 to 600 kg in gross weight. The tow is peeled off from the bale and opened in a wide belt-like form of desired size and bulk. An opening width of the tow can be arbitrarily decided, for example 50 to 2,000 mm, preferably about 50 to 300 mm, so as to be adapted to the width of the absorbent body in the product. In addition, the density of the absorbent body can be adjusted by controlling a degree of tow opening.

Preferably, high-absorbent polymer particles 54, 54 . . . are contained in the absorbent body 56, as shown in FIG. 2. In addition, at least in an area receiving a fluid, high-absorbent polymer particles (SAP particles) are desirably scattered in a virtually overall thickness direction with respect to the assembly of filaments 52, 52 . . . . FIG. 2 is a conceptual enlarged view of the particles scattered in the virtually overall thickness direction.

If there are no or few if any, SAP particles in upper, lower and intermediate portions of the absorbent body 56, it is not recognized that "the SAP particles are scattered in the overall thickness direction". Therefore, the "scattered in the overall thickness direction" state refers to a mode in which the particles are scattered "evenly" in the overall thickness direction with respect to the assembly of filaments, or a mode in which the particles are "unevenly distributed" in the upper, lower and/or intermediate portions but still are scattered in the upper, lower and/or intermediate portions. In addition, the foregoing state does not exclude a mode in which some of the SAP particles does not enter into the assembly of filaments 52, 52 . . . and remain on a surface of the same, or a mode in which some of the SAP particles pass through the assembly of filaments 52, 52 . . . and exist on the envelope sheet 58 or the holding sheet 80.

(High-Absorbent Polymer Particles)

The high-absorbent polymer particles 54 may be not only "particles" but also "powders". A particle diameter of the high-absorbent polymer particles 54 may be the same as that of particles used in this kind of absorbent articles, and is 1,000 μm or less, desirably in particular 150 to 400 μm. There are no particular limits on a material for the high-absorbent polymer particles 54, and a preferred material is 40 g/g or more in capacity of water absorption. The high-absorbent polymer particles 54 may be based on starch, cellulose or synthetic polymer, and may use starch-acrylic acid (salt) graft copolymer, saponified product of starch-acrylonitrile copolymer, cross-linked sodium carboxymethyl cellulose, acrylic acid (salt) polymer, or the like. A shape of the high-absorbent polymer particles 54 is preferably a commonly used particulate shape, and may also be any other shape.

The high-absorbent polymer particles 54 preferably deliver a water absorption speed of 40 seconds or less. If the water absorption speed exceeds 40 seconds, a backflow phenomenon becomes prone to occur, where a fluid supplied to the absorbent body 56 flows back out of the absorbent body 56.

In addition, the high-absorbent polymer particles 54 are preferably 1,000 Pa or more in gel strength. This prevents effectively a sticky feel after absorption of a fluid even if the absorbent body 56 is high in bulk.

A basis weight of the high-absorbent polymer particles 54 may be decided as appropriate in accordance with an absorption capacity required for the absorbent body 56, and may be 50 to 350 g/m$^2$, although it is not always defined so. If the basis weight of the polymers is less than 50 g/m$^2$, it is difficult to ensure a sufficient absorption capacity. If the basis weight exceeds 350 g/m$^2$, the high-absorbent polymer particles 54 become saturated in effectiveness and an excessive amount thereof has an unpleasant grainy feel.

If necessary, the high-absorbent polymer particles 54 can be adjusted in density or amount of dispersion in the planar direction of the absorbent body 56. For example, an amount of dispersion may be made larger at a fluid excreted portion than other portions. With regard to a difference between the sexes, the dispersion density (amount) may be increased at the front portion for men or increased at the central portion for women. The absorbent body 56 may have a local portion (in spot, for example) with no polymer in the planer direction thereof.

As needed, a plurality of high-absorbent polymer particles 54 with different particle size distributions can be provided in sequence in the thickness direction, such that the particles with smaller particle size distributions are located on the lower portion of the absorbent body 56, and the particles with larger particle size distributions on the upper portion of the same.

Proportions of the high-absorbent polymer particles 54 and the continuous fibers affect an absorbing property. A weight ratio of the high-absorbent polymer particles to the continuous fibers in a planar area of 5×5 cm directly receiving a fluid in the absorbent body 56, is 1 to 14, desirably 2 to 9 in particular.

(Envelope Sheet)

The envelope sheet 58 may use any of materials such as tissue paper, particularly crepe paper, nonwoven fabrics, polyethylene-laminated nonwoven fabrics, foraminous sheets, and the like. The sheet desirably does not let high-absorbent polymer particles pass through. In using a nonwoven fabric instead of crepe paper for the envelope sheet 58, a hydrophilic SMMS (spun bonded/melt-blown/melt-blown/spun-bonded) nonwoven fabric is preferred in particular. A material for such a fabric may be polypropylene, polyethylene/polypropylene, or the like. A basis weight of the fabric is 5 to 40 g/m$^2$, desirably 10 to 30 g/m$^2$ in particular.

The envelope sheet 58 may be configured as to envelop an overall layer containing the assembly of continuous fibers 52, 52 . . . and the high-absorbent polymer particles 54, 54 . . . as shown in FIG. 2, or may envelop only under and side surfaces of the layer. Further, although not shown, the envelope sheet 58 may be configured as to cover the upper and side surfaces of the absorbent body 56 with crepe paper or a nonwoven fabric, and cover the under surface of the same with a liquid impervious sheet of polyethylene or the like, or as to cover the upper surface of the absorbent body 56 with crape paper or nonwoven paper and cover the side and under surfaces of the same with a liquid impervious sheet of polyethylene or the like (the foregoing materials are constitutional elements of the envelope sheet). If necessary, the envelope sheet 58 may be configured in such a manner that the layer containing the assembly of continuous fibers 52, 52 . . . and the high-absorbent polymer particles 54, 54 . . . is sandwiched between two upper and lower sheets, or in such a manner that one sheet is disposed only on the lower surface of the layer. However, these configurations are not desired because they make it difficult to prevent movement of the high-absorbent polymer particles.

(Holding Sheet)

In providing the holding sheet 80, the high-absorbent polymer particles 54 may be interposed by dispersing or the like between the holding sheet 80 and the absorbent body 56. The high-absorbent polymer particles 54 may pass through the assembly of the continuous fibers 52 during a process of supply to the assembly of the continuous fibers 52, a process subsequent to the foregoing process, or a process of distribution to consumers. The high-absorbent polymer particles having passed through the assembly of continuous fibers may bring an unpleasant grainy feel with asperities thereof to a user who touches the product by hand. To solve this problem, it is preferred to interpose the holding sheet 80 capable of holding the high-absorbent polymers 54 between the absorbent body 56 and the envelope sheet 58. The holding sheet 80 increases elasticity which would not be sufficiently provided by the envelope sheet 58 alone made of tissue paper (crepe paper) or the like, and reduces or prevents an unpleasant feel given to a user who touches the product by hand.

There is no particular limitation on a material for the holding sheet 80, and such a material only needs to be capable of holding the high-absorbent polymers 54. Specifically, the material may be any of nonwoven fabrics, crimped pulp, low-absorbent cotton fibers (e.g. fat cotton fibers, defatted cotton fibers, rayon fibers processed with a water repellent agent or a hydrophobizing agent), polyethylene fibers, polyester fibers, acrylic fibers, polypropylene fibers, silk, cotton, linen, nylon, polyurethane, acetate fibers, and the like, for example.

If the holding sheet 80 is formed by a nonwoven fabric, the holding sheet 80 is 0.01 to 10.00 gfcm/cm$^2$, preferably 0.01 to 1.00 gfcm/cm$^2$ in compression energy, and is 10 to 100%, preferably 70 to 100% in compression resilience, on the basis of test results from KES Test.

A purpose of providing the holding sheet 80 is, as stated above, to hold the high-absorbent polymers 54 which have dropped (slipped) downward from the absorbent body 56, for example. Therefore, the dropped high-absorbent polymers 54 come into contact with a user via the envelope sheet 58 and the holding sheet 80, and thus there is no fear of giving the user an unpleasant grainy feel. In particular, the nonwoven fabric within the above-mentioned ranges of compression energy and compression resilience can perform sufficiently function thereof.

In addition, since the slipped high-absorbent polymers 54 are held by the holding sheet 80 and thus do not move over the envelope sheet 58, there is no fear of uneven absorption capabilities. Particularly, to prevent movement of the high-absorbent polymer particles 54 over the holding sheet 80, the holding sheet 80 may be coated in advance with a sticky hot-melt adhesive or the like. Alternatively, to prevent movement of the high-absorbent polymer particles 54 over the holding sheet 80, the upper surface of the holding sheet 80 (facing to the usage surface of the absorbent body 56) may be made rough. For this purpose, the nonwoven fabric may be manufactured in such a manner that a surface thereof is roughed or fluffed by making non-netted, marbling, needle-punching, or brushing.

The holding sheet 80 may be provided only underneath the absorbent body 56 as shown in FIG. 2, or may pass by the absorbent body 56, roll and extend to the upper surface of the absorbent body 56, although not shown. In addition, a stack of a plurality of holding sheets 80 may be used.

Although, in the above example, the holding sheet 58 is disposed between the absorbent body 56 and the envelope sheet 58 on the lower side, the holding sheet may be placed under the envelope sheet instead (this arrangement is not shown). The important point is that providing the holding sheet 80 under the absorbent body 56 reduces or eliminates an unpleasant grainy feel which would be given to a user who touches the product from the under surface thereof.

(Crotch Outer Sheet)

The crotch outer sheet 12M is provided on the under surface of the absorber 20 and exposed on the external surface of the product. A material for the crotch outer sheet 12M may be the same as those of the ventral-side outer sheet 12F and the back-side outer sheet 12B, or may be one having higher strength or a deodorant differently from those of the ventral-side outer sheet 12F and the back-side outer sheet 12B. More specifically, the material may be any of various nonwoven fabrics such as a spun-bonded nonwoven fabric, a melt-blown nonwoven fabric, a point-bonded nonwoven fabric, an air-through nonwoven fabric, an air-point nonwoven fabric, a spun-lace nonwoven fabric, and an SMS nonwoven fabric, which are formed by fibers of PP, PP/PE, or PP/PET, or any of the foregoing nonwoven fabrics to which a deodorant or the like is added.

When a wearer is in a sitting position, a high body pressure is applied to the crotch outer sheet 12M. Accordingly, the crotch outer sheet 12M is preferably made of a material with high fastness to rubbing (causing no fluff), in particular, a material which has received a rating of "⊚" or "○" in testing for fastness to rubbing described below.

(Fastness-to-Rubbing Test)

Fastness to rubbing is pursuant to JIS L 0849 and is measured by a method explained below: a 250×25-mm sheet piece for measurement of fastness to rubbing is prepared, and a fastness to rubbing of the sheet piece is measured on an outer surface (outer surface of an absorber). Fastness to rubbing can be measured by a color fastness rubbing tester (produced by Tester Sangyo Co., Ltd., model: AB-301). In the measurement, the friction tester II type is used to vibrate the sheet piece 50 times. After the test, the resultant sheet piece is visually compared with a limit sample, and is rated on four scales ⊚: non-occurrence of both of twisted balls and fluff, ○: non-occurrence of twisted balls and occurrence of fluff, Δ: occurrence of both of twisted balls and fluff, and x: breakage of nonwoven fabric).

The crotch outer sheet 12M may include some design elements prepared by printing or coloring. In combination with the above-mentioned design sheet, the crotch outer sheet 12M and the design sheet are preferably arranged such that the design matters on the two sheets do not overlap.

The crotch outer sheet 12M preferably uses a resilient and elastic nonwoven fabric which is extended and attached in a longitudinal direction to the absorber 20, thereby increasing a fit at the crotch portion.

If the absorbent body 56 is an ultra-thin absorbent body which is 100 g/m² or less in fiber basis weight and is 100 g/m² or more in high-absorbent polymer basis weight, the absorbent body 56 has no significant elasticity and needs to be made more elastic at the crotch portion while avoiding deterioration in easiness to wear. Meanwhile, the absorbent body 56 does not need to be so elastic at the ventral and back sides. Therefore, in such an arrangement, the crotch outer sheet 12M preferably uses a sheet with high stiffness (elasticity). More specifically, the crotch outer sheet 12M uses preferably a sheet in which a sum of bending resistance values in machine direction and cross direction measured by the Clark process (JIS L1096 C process) is 100 mm or more, preferably 150 mm or more.

In the illustrated example, the crotch outer sheet 12M is sandwiched between the absorber 20 and the ventral- and back-side outer sheets 12F, 12B at sections in which the ventral- and back-side outer sheets 12F, 12B and the absorber 20 overlap each other. Alternatively, the crotch outer sheet 12M may be attached to outside the ventral- and back-side outer sheets 12F, 12B. The crotch outer sheet 12M is attached to the under surface of the absorber 20 and the inner surfaces or outer surfaces of the ventral- and back-side outer sheets 12F and 12B by a hot-melt adhesive or the like.

(Others)

In the foregoing embodiment, the ventral-side outer sheet 12F is composed of only an area corresponding to the joined sections 12A in the up-down direction. Alternatively, the ventral-side outer sheet 12F may include a ventral-side main unit section corresponding to the joined sections 12A in the up-down direction, and a ventral-side extension section extending under the ventral-side main unit section and having no resilient and elastic members. Such an arrangement allows the ventral-side outer sheet 12F to be fitted to a wearer around the legs along the groin. In this arrangement, an area of the ventral-side extension section is preferably 10 to 80% of an area of the back-side extension section, more preferably 20 to 50% of the same. The excessively large ventral-side extension section is not preferred due to a deteriorated fit property.

EXAMPLES

FIG. 10 shows a configuration of the elongated resilient and elastic members 15 to 18, 19T, and 19U in an example of the present invention, a position of the joined sections 12A when the diaper is fitted to a wearer, and an inclination angle of the joined sections to be obtained according to a joined section inclination test. FIG. 11 shows a configuration of the elongated resilient and elastic members in a comparative example, a position of the joined sections 12A when the diaper is fitted to a wearer, and an inclination angle of the joined sections to be obtained according to a joined section inclination test. In each of the diagrams, a trajectory of the joined sections 12A is indicated with circles. The resilient and elastic members are all made of the same synthetic rubber. The back-side outer sheet 12B and the ventral-side outer sheet 12F are formed of two nonwoven fabrics with a basis weight of 20 g/m² which are stuck to each other with a hot-melt adhesive, with elongated resilient and elastic members sandwiched therebetween at predetermined positions. As understood from a comparison between the two diagrams, according to the present invention, the joined sections between the back-side outer sheet and the ventral-side outer sheet are less prone to be shifted in position toward the back side with increasing proximity to the lower ends when the diaper is being used.

Second Embodiment

FIGS. 13 to 16 show one example of an underpants type disposable diaper in a second invention. This example will be described below centering on differences from the first embodiment. Identical components in the second embodiment and the first embodiment are given the same reference numerals.

In the underpants type disposable diaper 10 of the second embodiment, the back-side main unit section 13 is conceptually divided in the up-down direction into an upper end portion (waist portion) W and a lower portion Z (equivalent to the lower end portion U and the intermediate portion M in the first embodiment) below the upper end portion W. An area of the lower portion Z varies on a product size, but in general, the lower portion Z may be 35 to 220 mm long in the up-down direction.

At the upper end portion (waist portion) W of the back-side main unit section 13, a plurality of back-side waist resilient and elastic members 17 is continuously fixed in the entire width direction at intervals in the up-down direction and in a state of being extended in the width direction at a predetermined extension ratio. In addition, out of the back-side waist resilient and elastic members 17, one or more arranged in an area adjacent to the lower portion Z of the back-side main unit section 13 may overlap the absorber 20 or may be arranged on both sides of the back-side main unit section 13 in the width direction except for the central portion in the width direction overlapping the absorber 20. The back-side waist resilient and elastic members 17 are preferably about 3 to 22 rubber threads that are about 155 to 1,880 dtex, in particular about 470 to 1,240 dtex in fineness (in the case of synthetic rubber. For natural rubber, about 0.05 to 1.5 mm², in particular about 0.1 to 1.0 mm² in cross-section area) and are arranged at intervals of 4 to 12 mm at an extension ratio of about 150 to 400%, in particular about 220 to 320%. Further, the back-side waist resilient and elastic members 17 do not need to be all the same in fineness and extension ratio, and may be different in fineness and extension ratio between the upper and lower sides of the back-side waist portion, for example. The back-side waist resilient and elastic members 17 can be freely set in fineness and extension ratio, regardless of magnitude relations with the first and second elongated resilient and elastic members 15, 16.

In the lower part Z of the back-side main unit section 13 except for the central portion in the width direction overlapping the absorber 20, a plurality of first elongated resilient and elastic members 15 is continuously fixed to areas above and on both sides of the central portion in the width direction, at intervals in the up-down direction and in a state of being extended in the width direction at a predetermined extension ratio.

As the first elongated resilient and elastic members 15, about 5 to 30 rubber threads with a fineness of about 155 to 1,880 dtex, in particular 470 to 1,240 dtex (in the case of synthetic rubber. For natural rubber, about 0.05 to 1.5 mm², in particular 0.1 to 1.0 mm², in cross-section area) are preferably fixed at intervals of 1 to 15 mm, in particular 3 to 8 mm, at an extension ratio of about 200 to 350%, in particular about 240 to 300%.

In the back-side extension section 14 except for the central portion in the width direction overlapping the absorber 20, a plurality of second elongated resilient and elastic members 16 is continuously fixed in the entire width direction to areas on both sides of the central portion in the width direction (at least covering the entire hip cover portions 14C), at intervals in the up-down direction and in a state of being extended in the width direction at a predetermined extension ratio.

As the second elongated resilient and elastic members 16, about 2 to 10 rubber threads with a fineness of about 155 to 1,880 dtex, in particular about 470 to 1,240 dtex (in the case of synthetic rubber. For natural rubber, about 0.05 to 1.5 mm², in particular about 0.1 to 1.0 mm² in cross-section area) are preferably fixed at intervals of 5 to 40 mm, in particular 5 to 20 mm, at an extension ratio of 150 to 300%, in particular 180 to 260%.

Characteristically, with reference to a portion corresponding to the lower ends of the joined sections 12A in the up-down direction, the first elongated resilient and elastic members 15 are not arranged in an area P1 above the portion up to 5 mm, and the second elongated resilient and elastic members are not arranged in an area P2 below the portion down to 10 mm. The first elongated resilient and elastic members 15 and the second elongated resilient and elastic members 16 can be arranged in any areas except for the areas P1, P2. Those elongated resilient and elastic members may be partly arranged in the areas P1, P2, but are preferably arranged in the substantially entire areas (where elastic forces of the members act entirely).

In a preferred arrangement, the contraction forces of the second elongated resilient and elastic members 16 become weaker with increasing proximity to the lower ends of the hip cover portions 14C. Specifically, the second elongated resilient and elastic members 16 closer to the lower ends of the hip cover portions 14C may be lowered in extension ratio, reduced in fineness, arranged at wider intervals, or use a material with weaker elastic forces, or may be configured in any combination of the foregoing methods. If the second elongated resilient and elastic members 16 are decreased in extension ratio with identical fineness, interval, and material, a range of decrease (for each position change of 1 mm in the up-down direction) may be from about 1 to 30%/mm for example, preferably from about 1 to 10%/mm. If the second elongated resilient and elastic members 16 are decreased in fineness with identical extension ratio, interval, and material, a range of decrease (for each position change of 1 mm in the up-down direction) may be from about 5 to 150 dtex/mm for example, preferably from about 5 to 50 dtex/mm.

Meanwhile, the ventral-side outer sheet 12F is preferably composed of only the ventral-side main unit section (corresponding to the joined sections 12A in the up-down direction), basically in a manner similar to the back-side main unit section 13 of the back-side outer sheet 12B. Therefore, the ventral-side outer sheet 12F takes the shape of a rectangle extending along the waist portion and has no extension section unlike the back-side outer sheet 12B having the back-side extension section 14. As a matter of course, the ventral-side outer sheet 12F may include a ventral-side main unit section corresponding to the joined sections 12A in the up-down direction, and a ventral-side extension section extending under the ventral-side main unit section and having no resilient and elastic members, as in the first embodiment. In that case, an arrangement of the ventral-side outer sheet 12F in the second embodiment is identical to that in the first embodiment.

Specifically, in the ventral-side outer sheet 12F (ventral-side main unit section) having the upper end portion (waist portion) W and the lower portion Z, a plurality of ventral-side waist resilient and elastic members 18 is continuously fixed in the entire width direction to the upper end portion W, at intervals in the up-down direction and in a state of being extended in the width direction at a predetermined extension ratio. The ventral-side waist resilient and elastic members 18 are preferably approximated as much as possible to the backside waist resilient and elastic members 17 in number, fineness, extension ratio, interval, and arrangement pattern in the up-down direction, but may be different from the same. In differentiating between those members, a difference in number is 10 or less, preferably 5 or less; a difference in fineness is 1,880 dtex or less, preferably 470 dtex or less; a difference in extension ratio is 100% or less, preferably 40% or less; and a difference in interval is 10 mm or less, preferably 5 mm or less.

Further, in the lower portion Z of the ventral-side outer sheet 12F (ventral-side main unit section) except for the central portion in the width direction overlapping the absorber 20, a plurality of third elongated resilient and elastic members 19 is continuously fixed in the entire width direction to areas above and on both sides of the central portion, at intervals in the up-down direction and in a state of being extended in the width direction at a predetermined extension ratio. The third elongated resilient and elastic members 19 may be partly arranged in the lower portion in the up-down direction, but are preferably arranged in the substantially entire lower portion (where contraction forces entirely act).

The third elongated resilient and elastic members 19 are preferably approximated as much as possible to the first elongated resilient and elastic members 15 in number, fineness, extension ratio, interval and arrangement pattern in the up-down direction, or may be different from the same. In differentiating between those members, a difference in number is 10 or less, preferably 5 or less; a difference in fineness is 1,880 dtex or less, preferably 470 dtex or less; a difference in extension ratio is 100% or less, preferably 40% or less; and a difference in interval is 10 mm or less, preferably 5 mm or less.

In the thus configured underpants type disposable diaper, contraction forces from the first and second elongated resilient and elastic members 15 and 16 in the back-side outer sheet 12B hardly affect the lower ends of the joined section 12A, as shown in FIG. 17, thereby not allowing the hip cover portions 14C to be swollen or curled. As a result, while the diaper is being used, the hip cover portions 14C become less prone to cause swelling and curling (refer to FIG. 18). In addition, since the second elongated resilient and elastic members 16 are configured in such a manner that contraction forces thereof become weaker with increasing proximity to the lower ends of the hip cover portions 14C, it is possible to prevent the hip cover portions 14C from being curled at the upper end and being excessively contracted at the lower ends.

Except for the configurations described above, the second embodiment is identical to the first embodiment, and the identical matters could be understood by those skilled in the art and thus description thereof will be omitted.

INDUSTRIAL APPLICABILITY

The present invention is applicable to an underpants type disposable diaper that is pre-formed in the shape of underpants.

BRIEF DESCRIPTION OF NUMERALS

Figure 1:
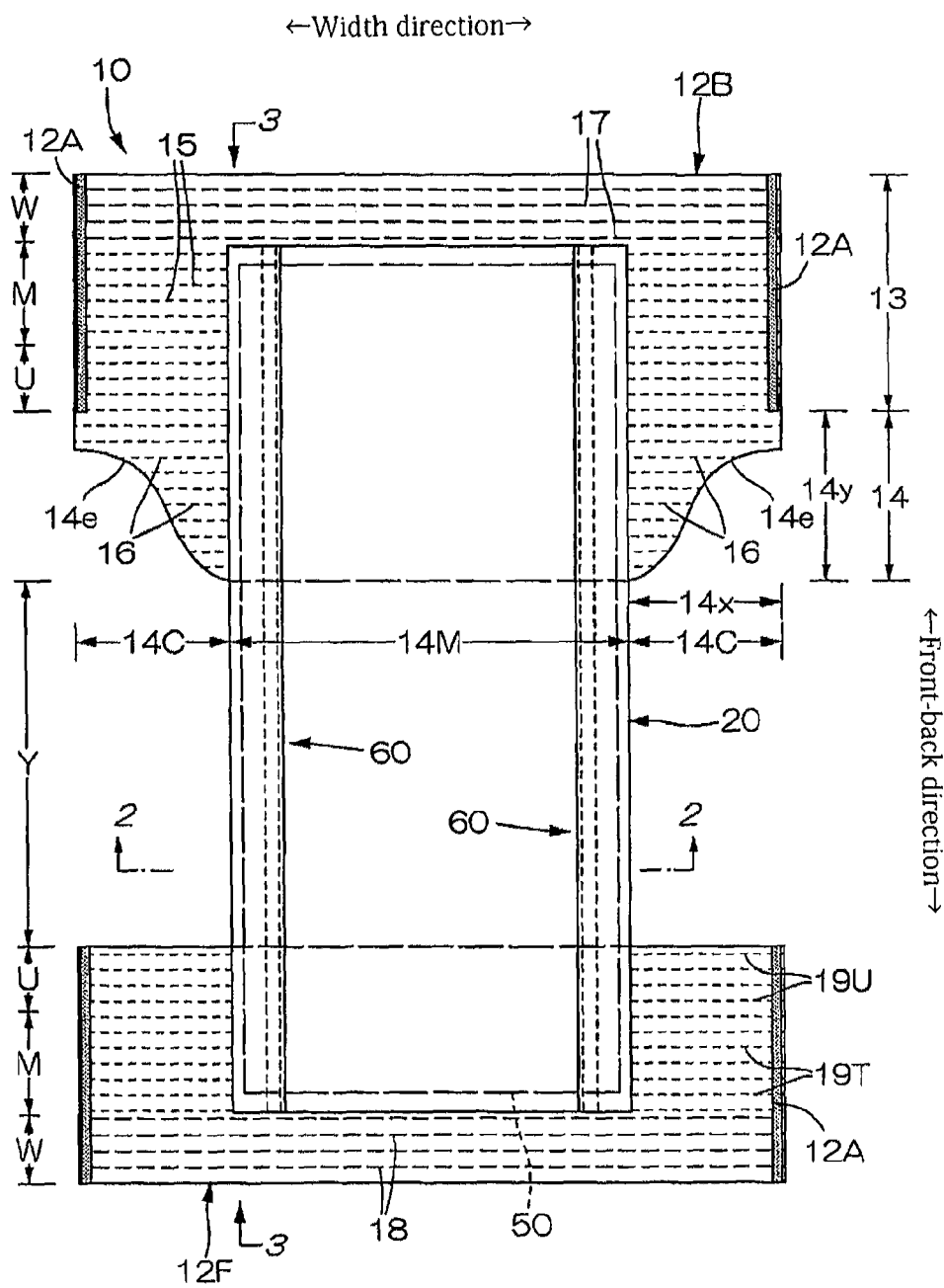
FIG. 1 is a plan view of an inner side of a first embodiment in an open state.
Figure 2:
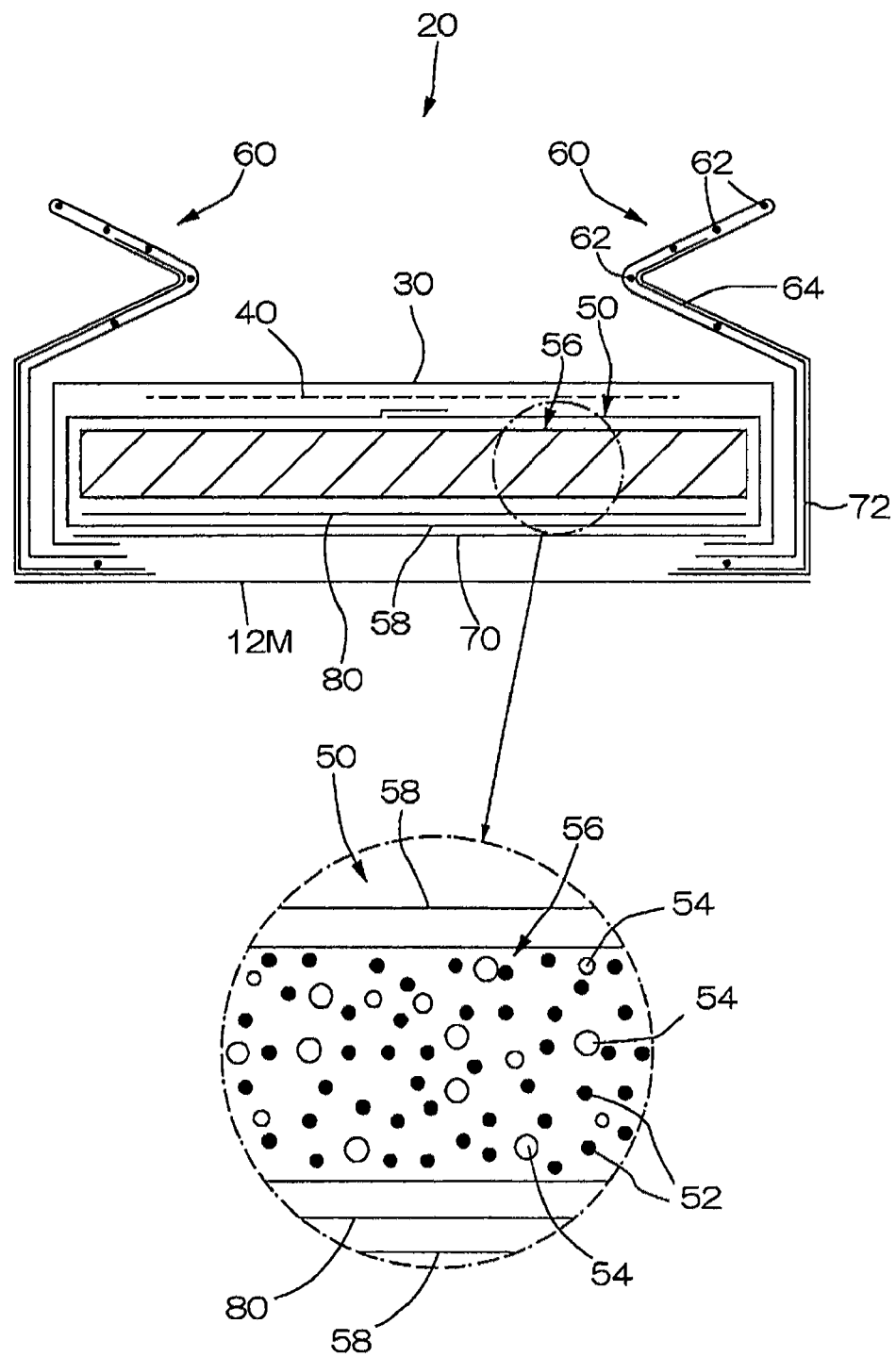
FIG. 2 is a cross-section view of FIG. 1 taken along line 2-2.
Figure 3:
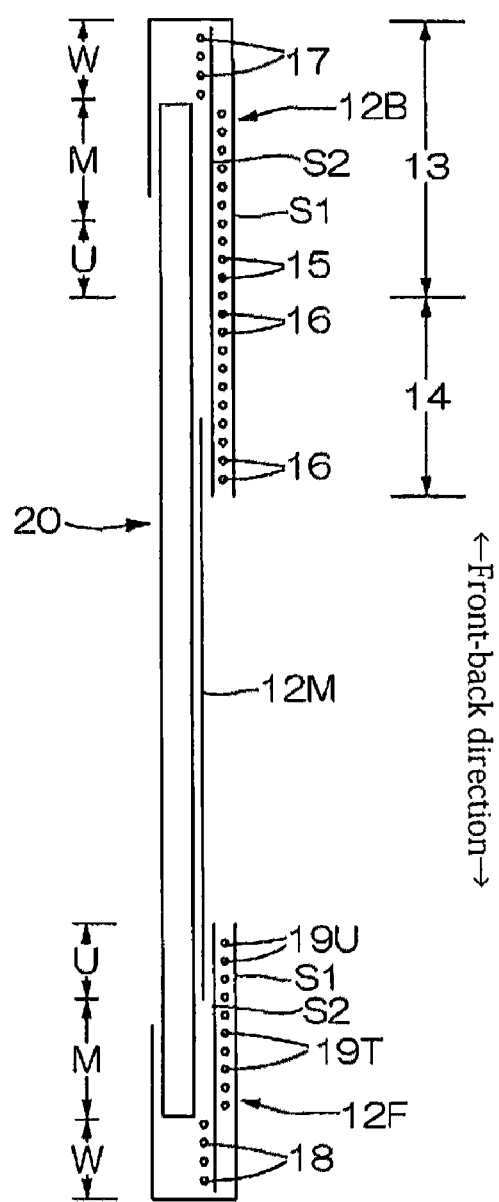
FIG. 3 is a cross-section view of FIG. 1 taken along line 3-3.
Figure 4:
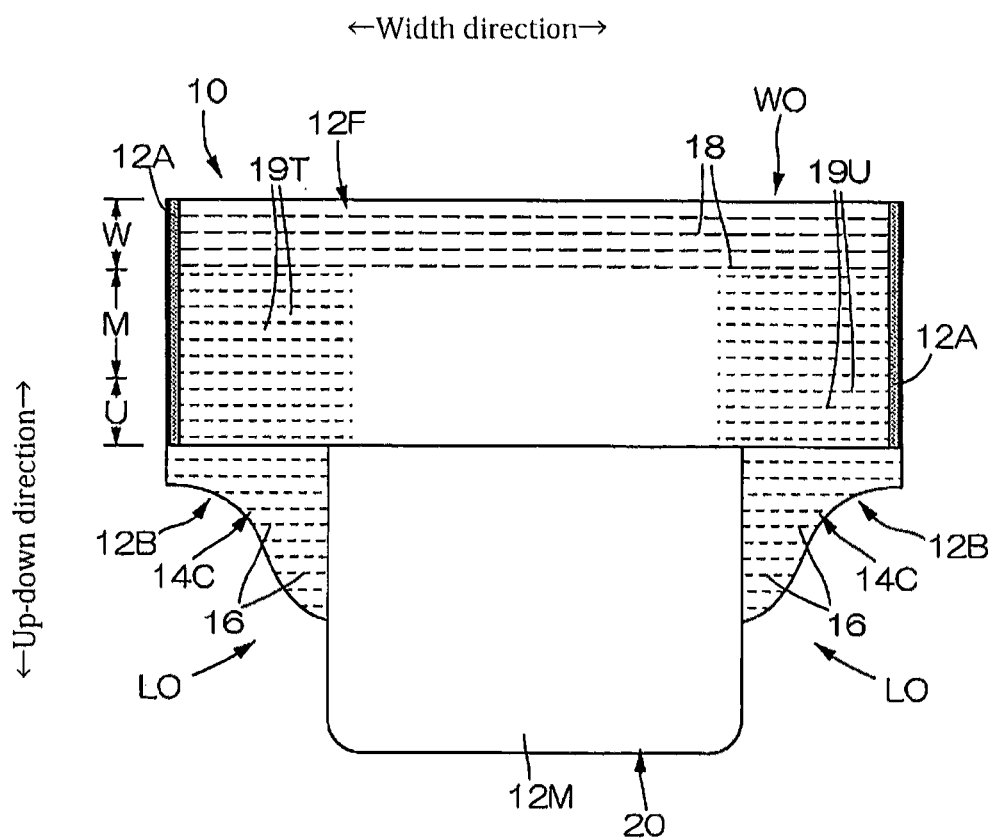
FIG. 4 is a front view of the first embodiment in a product state.
Figure 5:
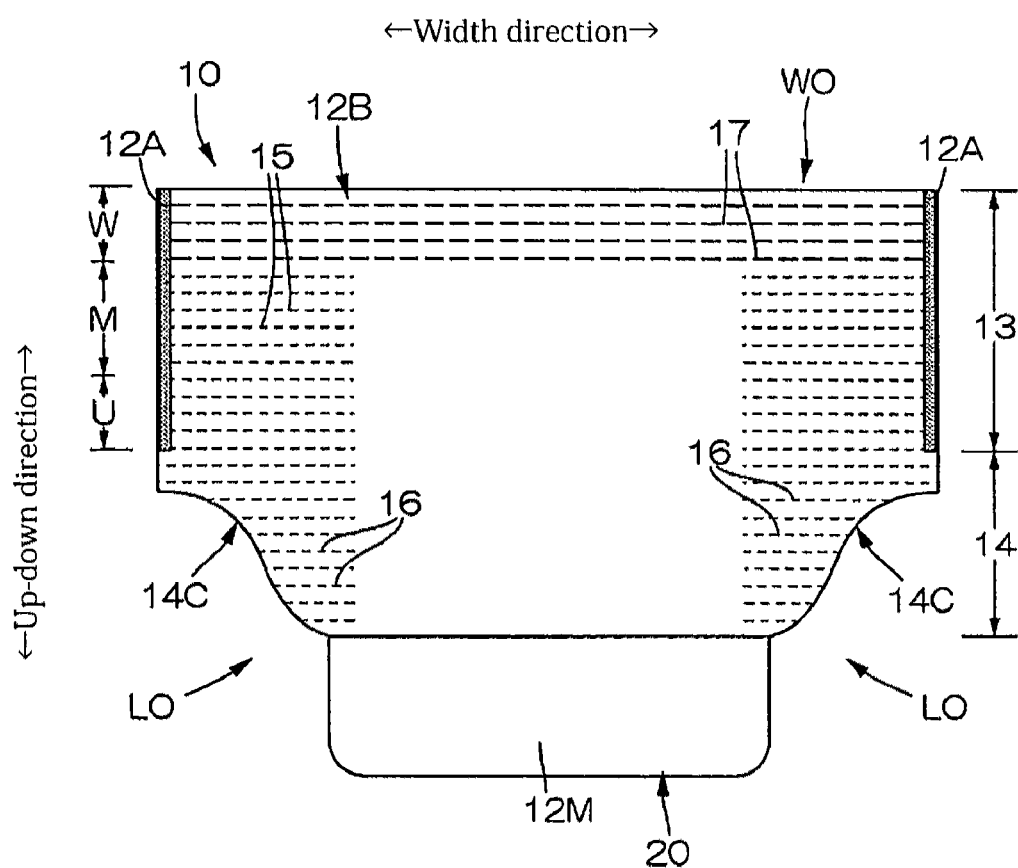
FIG. 5 is a rear view of the first embodiment in a product state.
Figure 6:
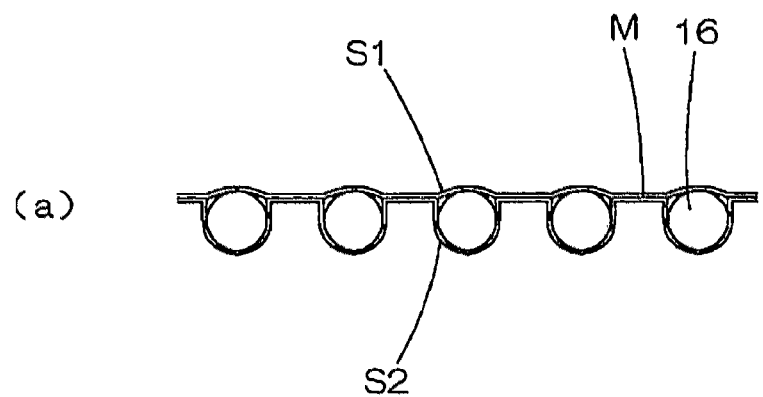
FIG. 6 is a schematic diagram showing a method for fixing resilient and elastic members by welding.
Figure 6:
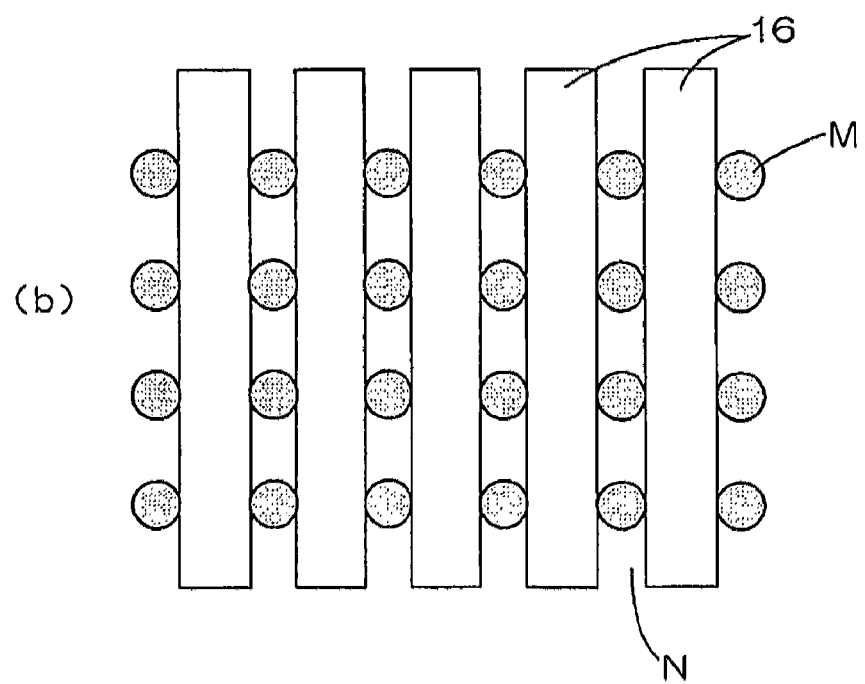
Figure 7:
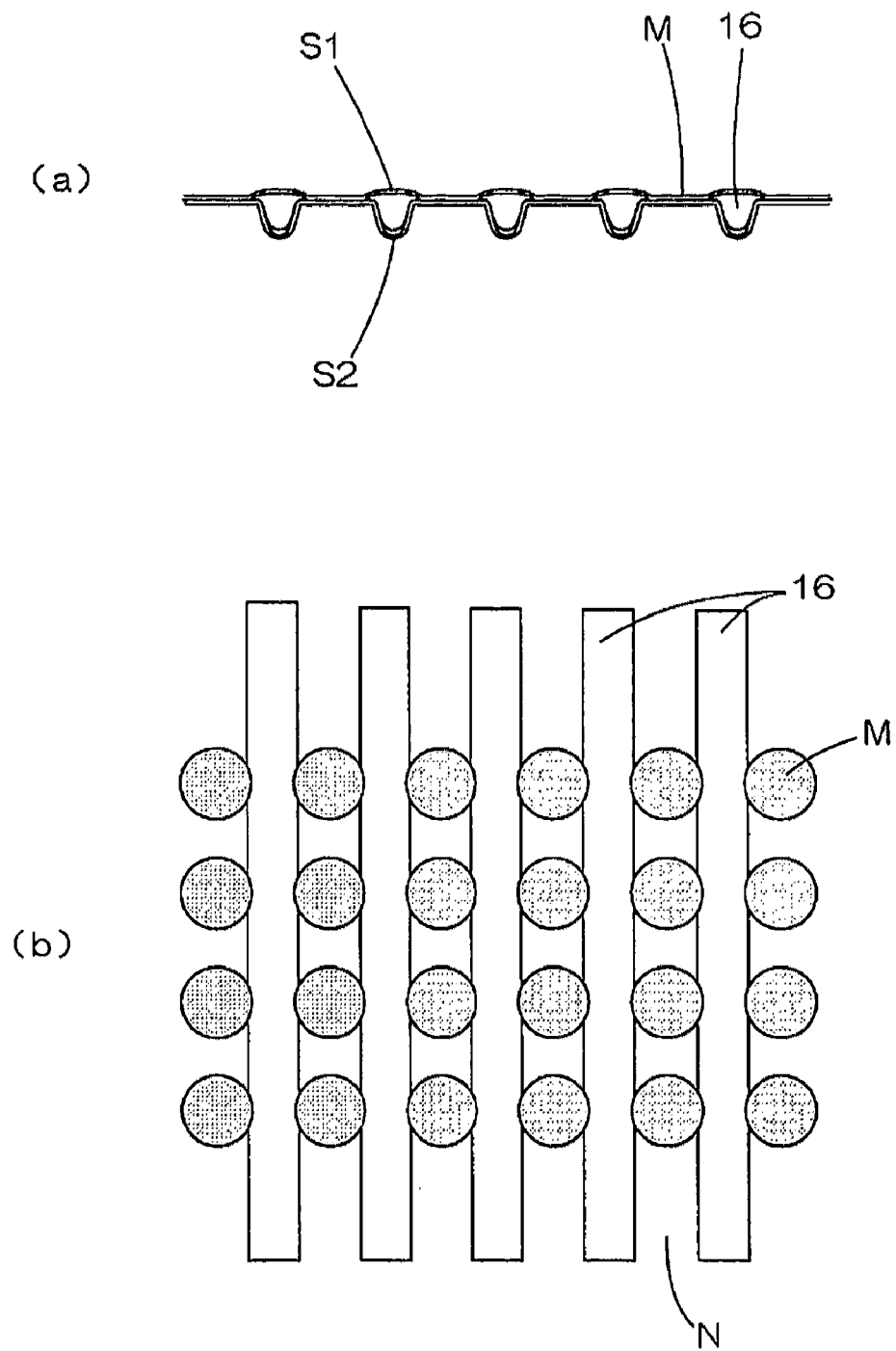
FIG. 7 is a schematic diagram showing another method for fixing resilient and elastic members by welding.
Figure 8:
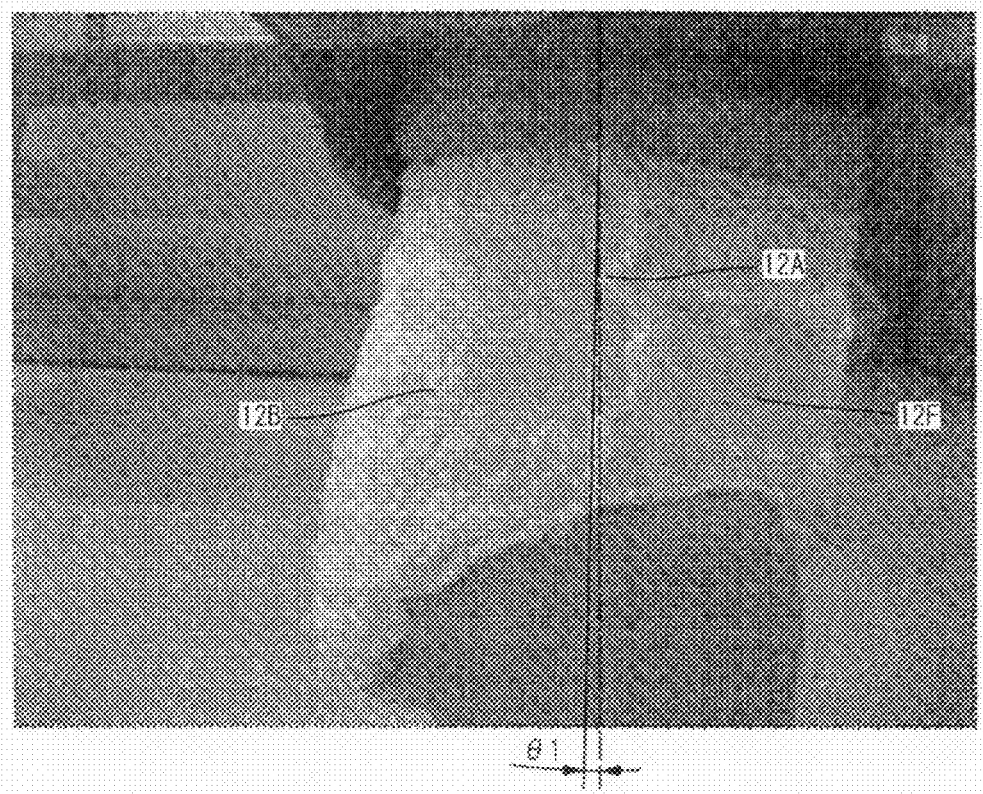
FIG. 8 is a photograph showing the first embodiment fitted to a wearer.
Figure 9:
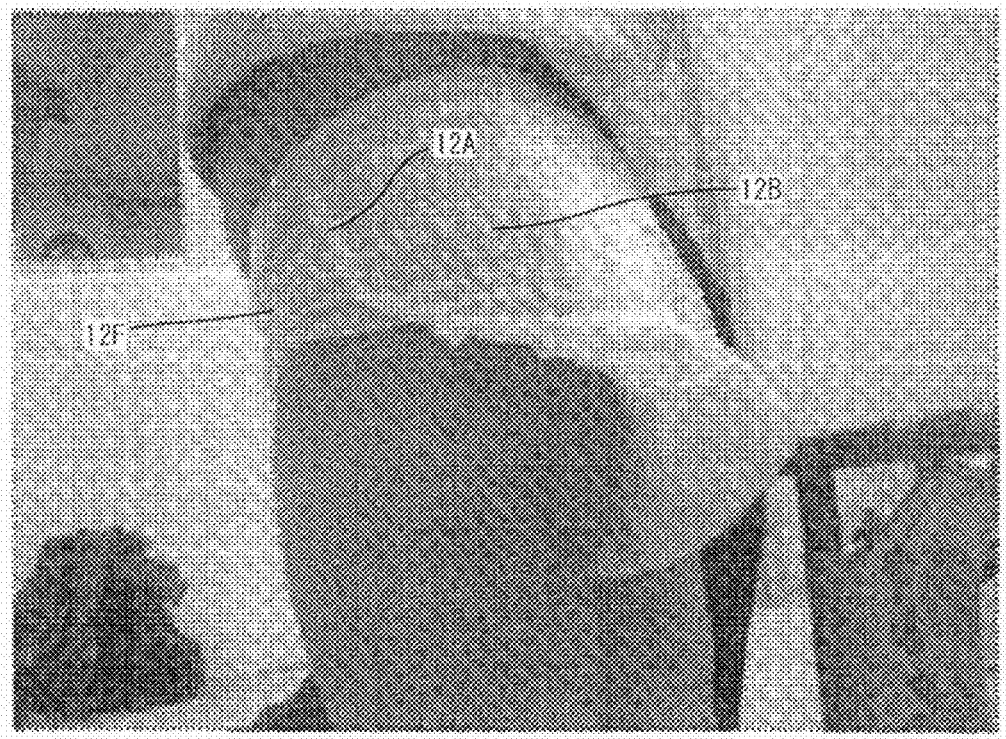
FIG. 9 is a photograph showing a comparative example fitted to a wearer.
Figure 10:
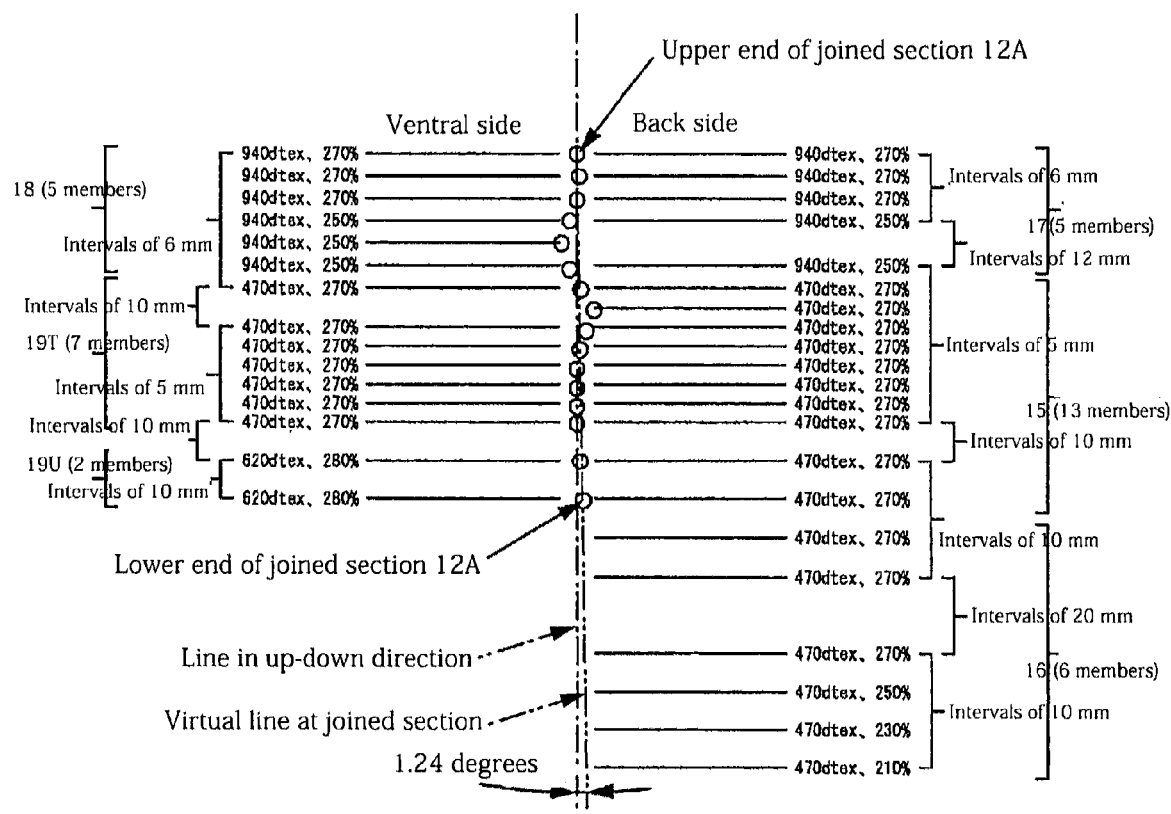
FIG. 10 is a diagram describing an example of the present invention with regard to a configuration of elongated resilient and elastic members, a position of a joined section when the example is fitted to a wearer, and an inclination angle of the joined section to be obtained according to a joined section inclination test.
Figure 11:
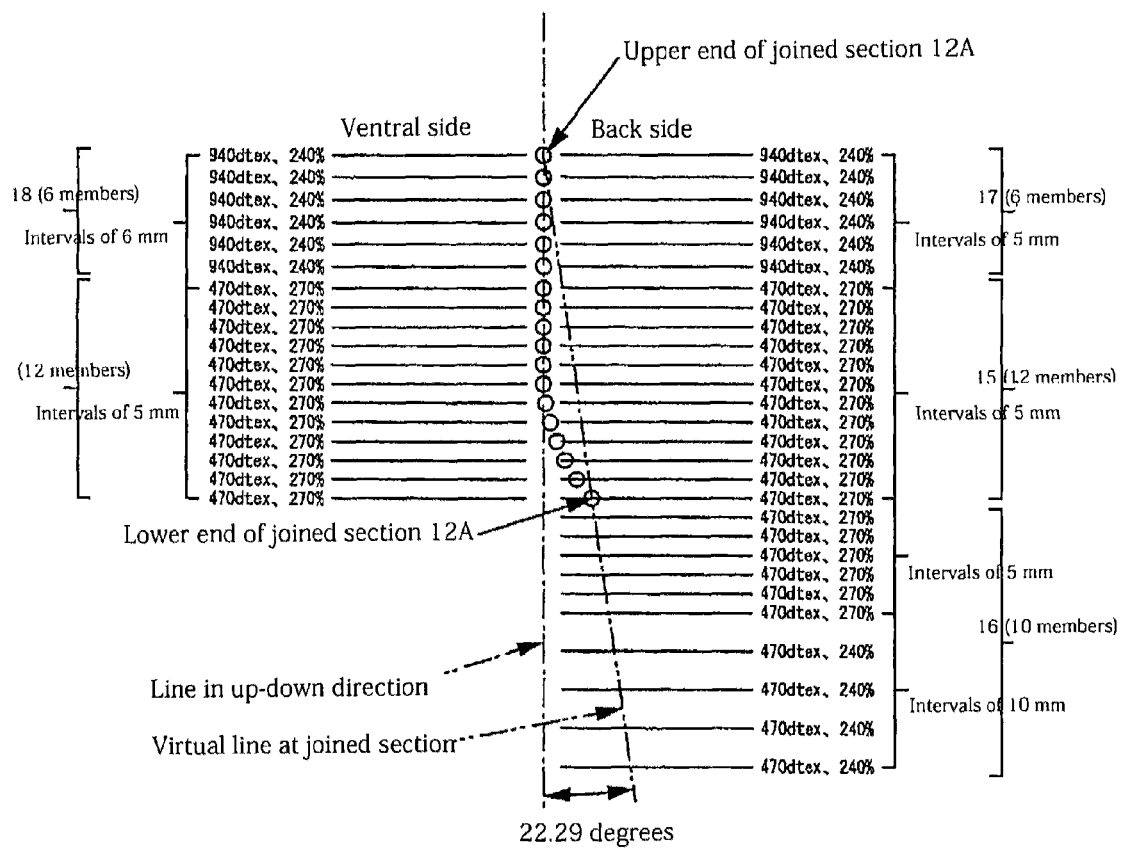
FIG. 11 is a diagram describing the comparative example with regard to a configuration of elongated resilient and elastic members, a position of a joined section when the comparative example is fitted to a wearer, and an inclination angle of the joined section to be obtained according to a joined section inclination test.
Figure 12:
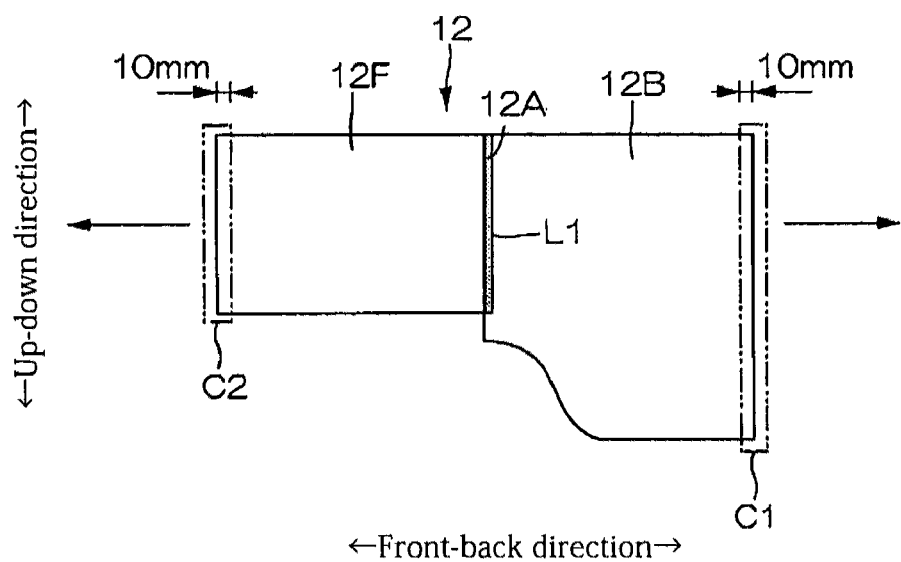
FIG. 12 is a schematic diagram showing how a joined section inclination test is carried out.
Figure 12:
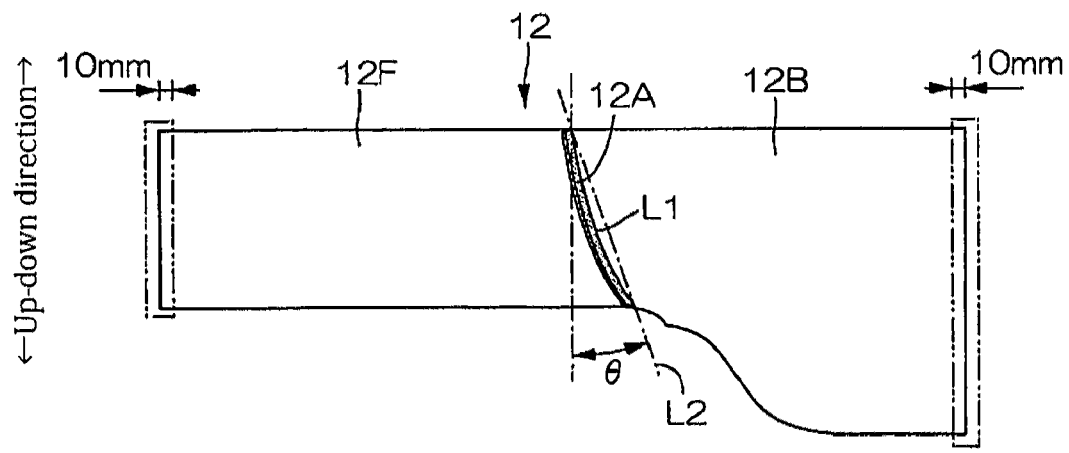
Figure 13:
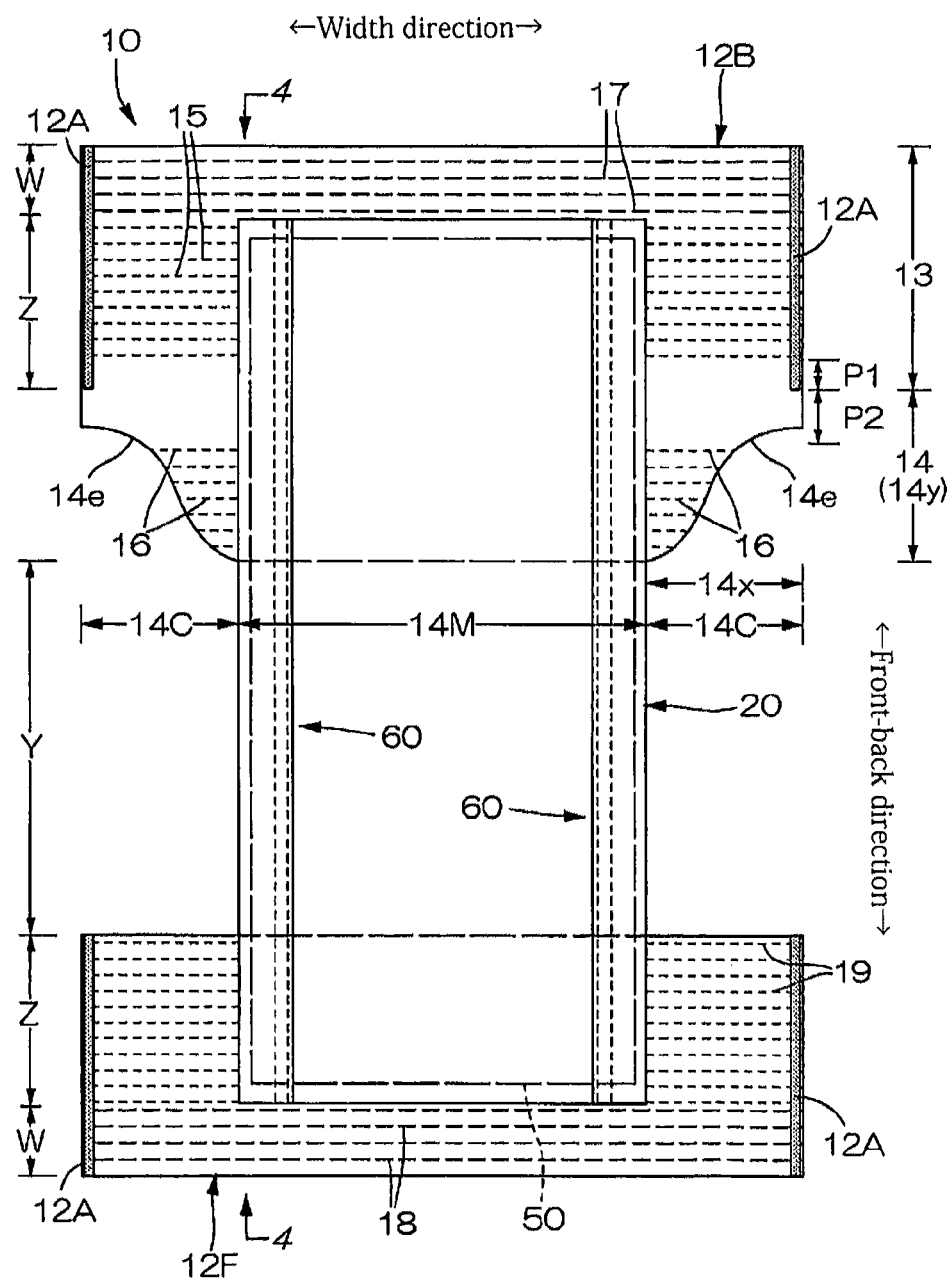
FIG. 13 is a plan view of an inner side of a second embodiment in an open state.
Figure 14:
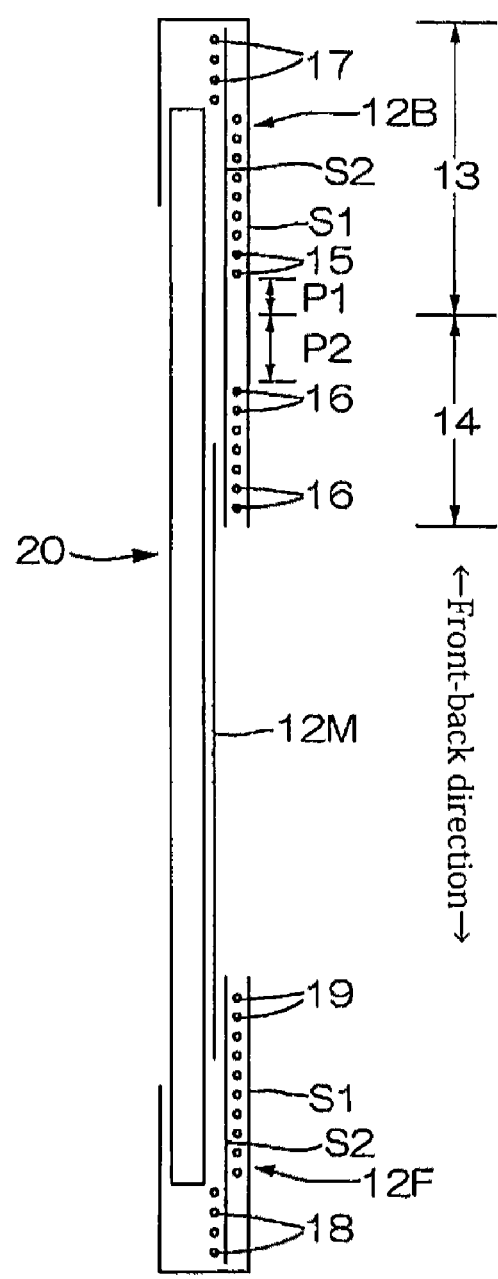
FIG. 14 is a cross-section view of FIG. 13 taken along line 4-4.
Figure 15:
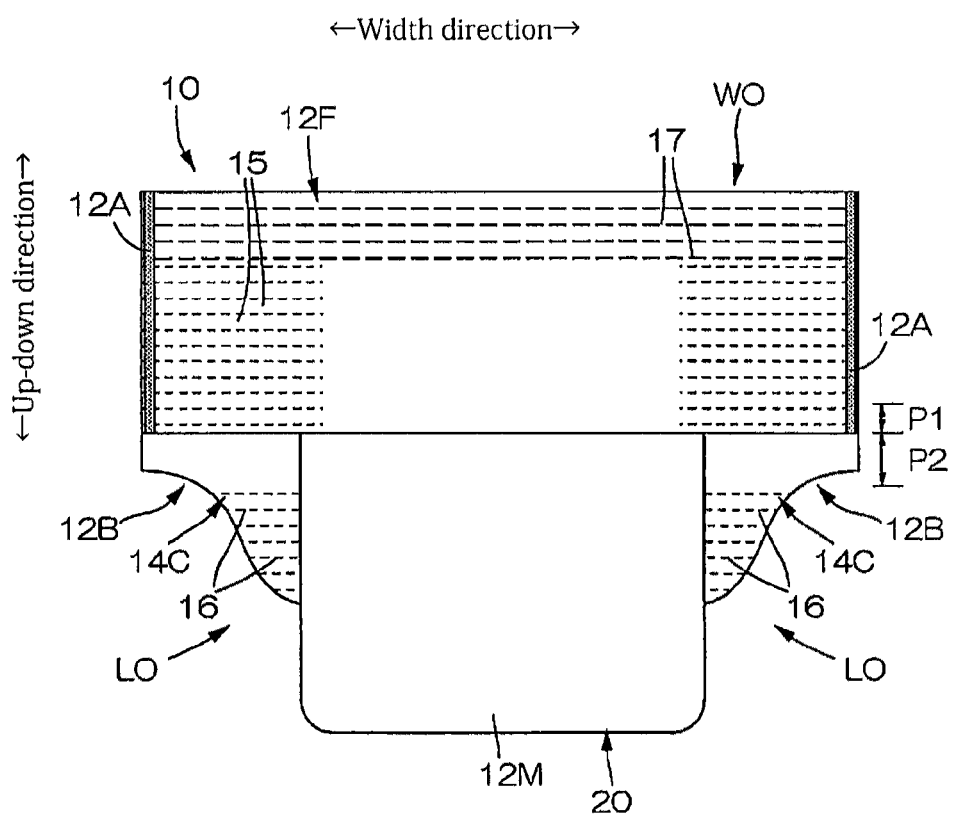
FIG. 15 is a front view of the second embodiment in a product state.
Figure 16:
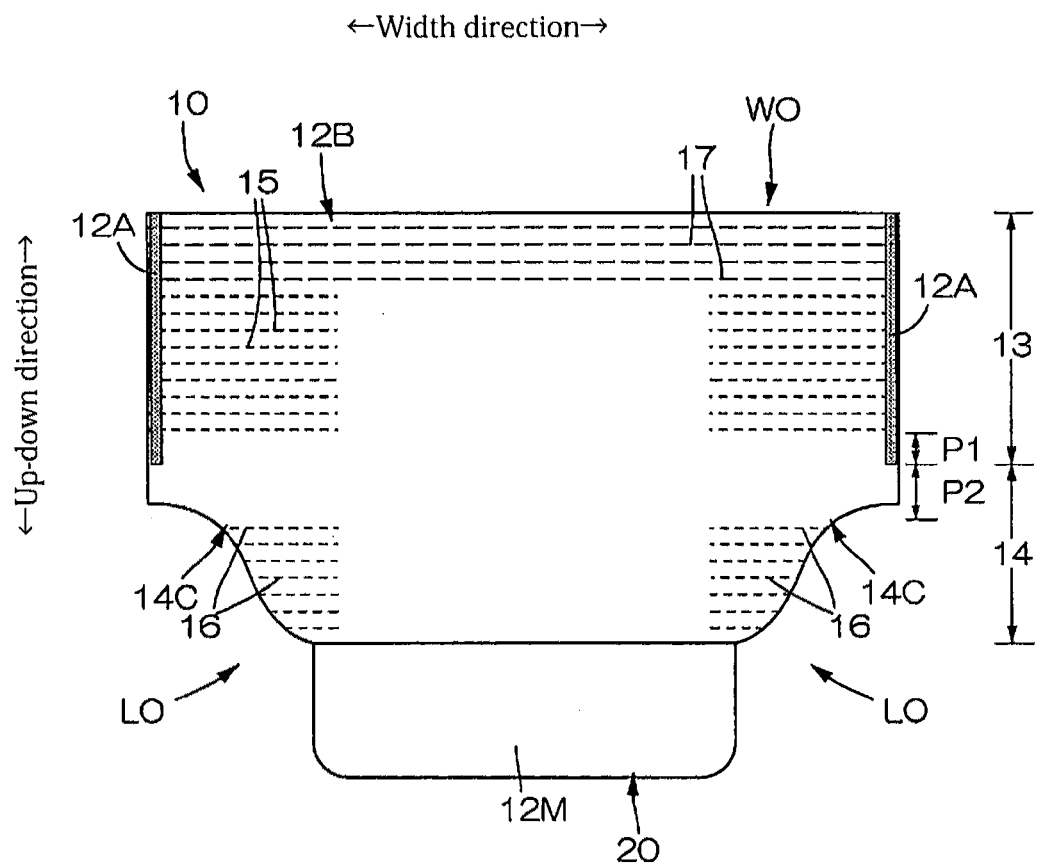
FIG. 16 is a rear view of the second embodiment in a product state.
Figure 17:
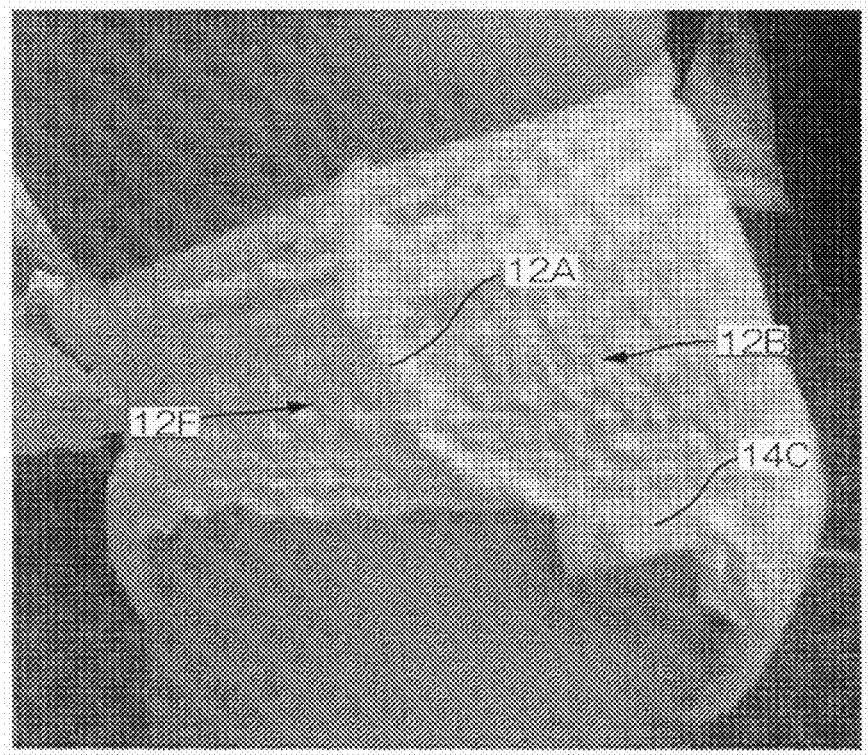
FIG. 17 is a photograph showing the second embodiment fitted to a wearer.
Figure 18:
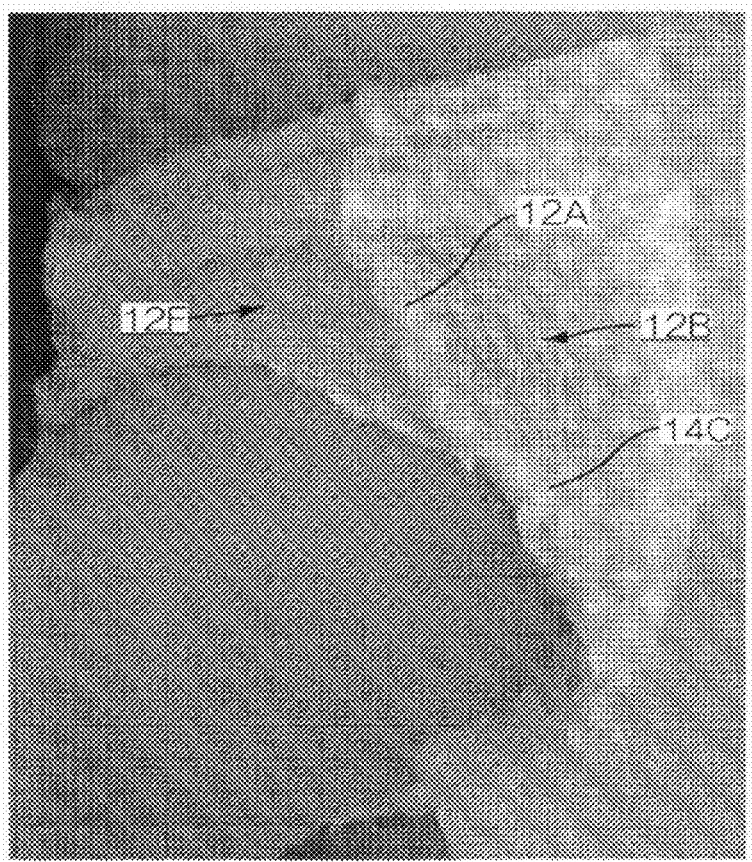
FIG. 18 is a photograph showing a comparative example fitted to a wearer.

10 . . . Absorber, 12 . . . Outer sheet, 12F . . . Ventral-side outer sheet, 12B . . . Back-side outer sheet, 13 . . . Back-side main unit section, 14 . . . Back-side extension section, 15 . . . First elongated resilient and elastic members, 16 . . . Second elongated resilient and elastic members

The invention claimed is:
1. An underpants type disposable diaper comprising:
a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction; and
an absorber that is connected at a front end portion to the ventral-side outer sheet on an inner surface at a central portion in the width direction and is connected at a back end portion to the back-side outer sheet on an inner surface at a central portion in the width direction, and covers the back side through crotch portion to the ventral side,
the ventral-side outer sheet and the back-side outer sheet being not connected but separated at the crotch portion, wherein
the back-side outer sheet has a back-side main unit section that corresponds to the joined sections in an up-down direction, and a back-side extension section that extends below the back-side main unit section, the back-side extension section has a central portion in the width direction overlapping the absorber and hip cover portions extending on both sides of the central portion, in the back-side outer sheet, the back-side main unit section has an upper end portion, a lower end portion, and an intermediate portion between the two end portions in the up-down direction, a plurality of back-side waist elongated resilient and elastic members is fixed to the upper end portion, at intervals in the up-down direction and in a state of being extended in the width direction at a predetermined extension ratio; a plurality of first elongated resilient and elastic members is fixed to the intermediate portion and the lower end portion at least in areas not overlapping the absorber, at intervals in the up-down direction and in a state of being extended in the width direction at a predetermined extension ratio; and a plurality of second elongated resilient and elastic members is fixed to at least the hip cover portions in the back-side extension section, at intervals in the up-down direction and in a state of being extended in the width direction at a predetermined extension ratio, the ventral-side outer sheet is composed of only a ventral-side main unit section that corresponds to the joined sections in the up-down direction, in the ventral-side outer sheet, the ventral-side main unit section has an upper end portion, a lower end portion, and an intermediate portion between the two end portions in the up-down direction, a plurality of ventral-side waist elongated resilient and elastic members is fixed to the upper end portion, at intervals in the up-down direction and in a state of being extended in the width direction at a predetermined extension ratio; a plurality of third elongated resilient and elastic members is fixed to the intermediate portion at least in areas not overlapping the absorber, at intervals in the up-down direction and in a state of being extended in the width direction at a predetermined extension ratio; and a plurality of fourth elongated resilient and elastic members is fixed to the lower end portion at least in areas not overlapping the absorber, at intervals in the up-down direction and in a state of being extended in the width direction at a predetermined extension ratio, and the back-side waist elongated resilient and elastic members, the ventral-side waist elongated resilient and elastic members, the first elongated resilient and elastic members, the second elongated resilient and elastic members, the third elongated resilient and elastic members, and the fourth elongated resilient and elastic members, are each specified in number, fineness, extension ratio, interval, kind of a material, and arrangement pattern in the up-down direction, such that an inclination angle of the joined sections is found to be 20 degrees or less according to a joined section inclination test, and wherein the back-side outer sheet and the ventral-side outer sheet are each formed by laminating two nonwoven fabrics with a basis weight of 10 to 30 g/m², a length of the lower end portion of the back-side main unit section and a length of the lower end portion of the ventral-side main unit section are equal and 30 to 100 mm in the up-down direction, the hip cover portions are 80 to 160 mm long in the width direction, and the hip cover portions are 30 to 80 mm long in the up-down direction, the first elongated resilient and elastic member in the lower end portion is 2 to 15 rubber threads made of synthetic rubber, 155 to 1,880 dtex in fineness and 200 to 350% in extension ratio, are arranged at intervals of 1 to 15 mm, the fourth elongated resilient and elastic members are 1 to 8 rubber threads made of synthetic rubber that are 155 to 1,880 dtex in fineness and 150 to 350% in extension ratio, and are arranged at intervals of 1 to 30 mm, and the second elongated resilient and elastic members are 2 to 10 rubber threads made of synthetic rubber that are 155 to 1,880 dtex in fineness and 150 to 300% in extension ratio, and are arranged at intervals of 5 to 40 mm.

2. The underpants type disposable diaper according to claim 1, wherein a contraction force per one second elongated resilient and elastic member is equal to or weaker than a contraction force per one first elongated resilient and elastic member, and a contraction force per one fourth elongated resilient and elastic member is equal to or stronger than a contraction force per one third elongated resilient and elastic member.

3. The underpants type disposable diaper according to claim 2, wherein contraction forces per constant width of the sections in the outer sheet meet a relationship: the lower end portion of the ventral-side main unit section≧the intermediate portion of the back-side main unit section>the intermediate portion of the ventral-side main unit section≧the lower end portion of the back-side main unit section and the back-side extension section.

4. The underpants type disposable diaper according to claim 1, wherein contraction forces per constant width of the sections in the outer sheet meet a relationship: the lower end portion of the ventral-side main unit section≧the intermediate portion of the back-side main unit section>the intermediate portion of the ventral-side main unit section≧the lower end portion of the back-side main unit section and the back-side extension section.

5. The underpants type disposable diaper according to claim 1, wherein a length of the upper end portion of the back-side main unit section and a length of the upper end portion of the ventral-side main unit section are equal and 15 to 80 mm in the up-down direction, a length of the intermediate portion of the back-side main unit section and a length of the intermediate portion of the ventral-side main unit section are equal and 30 to 100 mm in the up-down direction, the back-side waist elongated resilient and elastic members and the ventral-side waist elongated resilient and elastic members are each 3 to 22 rubber threads that are made of synthetic rubber, 155 to 1,880 dtex in fineness and 150 to 400% in extension ratio, and are arranged at intervals of 4 to 12 mm, and the first elongated resilient and elastic members in the intermediate portion and the third elongated resilient and elastic members are each 3 to 15 rubber threads that are made of synthetic rubber, 155 to 1,880 dtex in fineness and 150 to 300% in extension ratio, and are arranged at intervals of 1 to 15 mm.

6. The underpants type disposable diaper according to claim 1, wherein the hip cover portions are shaped, at outer edges in the width direction in a straight line or curved line approaching the absorber with increasing proximity to the crotch portion, and contraction forces of the second elongated resilient and elastic members acting on the hip cover portions become weaker with increasing proximity to the lower ends of the hip cover portions.

7. An underpants type disposable diaper comprising:
a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction; and
an absorber that is connected at a front end portion to the ventral-side outer sheet on an inner surface at a central portion in the width direction and is connected at a back end portion to the back-side outer sheet on an inner surface at a central portion in the width direction, and covers the back side through crotch portion to the ventral side,
the ventral-side outer sheet and the back-side outer sheet being not connected but separated at the crotch portion, wherein
the back-side outer sheet has a back-side main unit section that corresponds to the joined sections in an up-down direction, and a back-side extension section that extends below the back-side main unit section,
the back-side extension section has a central portion in the width direction overlapping the absorber and hip cover portions extending on both sides of the central portion or is composed of a ventral-side main unit section that corresponds to the joined section in the up-down direction and a ventral-side extension section that extends below the ventral-side main unit section and has no resilient and elastic members,
in the back-side outer sheet, the back-side main unit section has an upper end portion, a lower end portion, and an intermediate portion between the two end portions in the up-down direction, a plurality of back-side waist elongated resilient and elastic members is fixed to the upper end portion, at intervals in the up-down direction and in a state of being extended in the width direction at a predetermined extension ratio; a plurality of first elongated resilient and elastic members is fixed to the intermediate portion and the lower end portion at least in areas not overlapping the absorber, at intervals in the up-down direction and in a state of being extended in the width direction at a predetermined extension ratio; and a plurality of second elongated resilient and elastic members is fixed to at least the hip cover portions in the back-side extension section, at intervals in the up-down direction and in a state of being extended in the width direction at a predetermined extension ratio,
the ventral-side outer sheet is composed of only a ventral-side main unit section that corresponds to the joined sections in the up-down direction,
in the ventral-side outer sheet, the ventral-side main unit section has an upper end portion, a lower end portion, and an intermediate portion between the two end portions in the up-down direction, a plurality of ventral-side waist elongated resilient and elastic members is fixed to the upper end portion, at intervals in the up-down direction and in a state of being extended in the width direction at a predetermined extension ratio; a plurality of third elongated resilient and elastic members is fixed to the intermediate portion at least in areas not overlapping the absorber, at intervals in the up-down direction and in a state of being extended in the width direction at a predetermined extension ratio; and a plurality of fourth elongated resilient and elastic members is fixed to the lower end portion at least in areas not overlapping the absorber, at intervals in the up-down direction and in a state of being extended in the width direction at a predetermined extension ratio, and the back-side waist elongated resilient and elastic members, the ventral-side waist elongated and elastic members, the first elongated resilient and elastic members, the second elongated resilient and elastic members, the third elongated resilient and elastic members, and the fourth elongated resilient and elastic members, are each specified in number, fineness, extension ratio, interval, kind of a material, and arrangement pattern in the up-down direction, such that an inclination angle of the joined sections is found to be 20 degrees or less according to a joined section inclination test, and wherein
in the back-side outer sheet, with reference to a portion corresponding to the lower ends of the joined sections in the up-down direction, the first elongated resilient and elastic members are not arranged in an area above the portion up to 5 mm, and the second elongated resilient and elastic members are not arranged in an area below the portion down to 10 mm.

8. The underpants type disposable diaper according to claim 7, wherein
the second elongated resilient and elastic members are all equal in fineness, interval, and material, and become lower in extension ratio at a decrease rate of 1 to 30%/mm with increasing proximity to the lower ends of the hip cover portions, or the second elongated resilient and elastic members are all equal in extension ratio, interval, and material and become decreased in fineness at a decrease rate of 5 to 150 dtex/mm with increasing proximity to the lower ends of the hip cover portions.

9. An underpants type disposable diaper, comprising:
a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction; and
an absorber that is connected at a front end portion to the ventral-side outer sheet on an inner surface at a central portion in the width direction and is connected at a back end portion to the back-side outer sheet on an inner surface at a central portion in the width direction, and covers the back side through crotch portion to the ventral side,
the ventral-side outer sheet and the back-side outer sheet being not connected but separated at the crotch portion, wherein
the back-side outer sheet has a back-side main unit section that corresponds to the joined sections in an up-down direction, and a back-side extension section that extends below the back-side main unit section,
the back-side extension section has a central portion in the width direction overlapping the absorber and hip cover portions extending on both sides of the central portion,
the back-side main unit section has an upper end portion and a lower portion below the upper end portion in the up-down direction, back-side waist elongated resilient and elastic members are fixed to the upper end portion, in a state of being extended in the width direction at a predetermined extension ratio; a plurality of first elongated resilient and elastic members is fixed to the lower portion at least in areas not overlapping the absorber, at intervals in the up-down direction and in a state of being extended in the width direction at a predetermined extension ratio; and a plurality of second elongated resilient and elastic members is fixed to at least the hip cover portions, at intervals in the up-down direction and in a state of being extended in the width direction at a predetermined extension ratio, the ventral-side outer sheet is composed of only a ventral-side main unit section that corresponds to the joined sections in the up-down direction or is composed of a ventral-side main unit section that corresponds to the joined sections in the up-down direction and a ventral-side extension section that extends below the ventral-side main unit section and has no resilient and elastic members, in the ventral-side outer sheet, the ventral-side main unit section has an upper end portion in the up-down direction and a lower portion below the upper end portion, a plurality of ventral-side waist elongated resilient and elastic members is fixed to the upper end portion, at intervals in the up-down direction and in a state of being extended in the width direction at a predetermined extension ratio; and a plurality of third elongated resilient and elastic members is fixed to the lower portion at least in an area not overlapping the absorber, at intervals in the up-down direction and in a state of being extended in the width direction at a predetermined extension ratio, and in the back-side outer sheet, with reference to a portion corresponding to the lower ends of the joined sections in the up-down direction, the first elongated resilient and elastic members are not arranged in an area above the portion up to 5 mm, and the second elongated resilient and elastic members are not arranged in an area below the portion down to 10 mm.

10. The underpants type disposable diaper according to claim 9, wherein the ventral-side outer sheet is composed of only the ventral-side main unit section, the back-side outer sheet and the ventral-side outer sheet are each formed by laminating two nonwoven fabrics with a basis weight of 10 to 30 g/m$^2$, a length of the lower portion of the back-side main unit section and a length of the lower portion of the ventral-side main unit section are equal and 35 to 220 mm in the up-down direction, the hip cover portions are 80 to 160 mm long in the width direction, and the hip cover portions are 30 to 80 mm long in the up-down direction, the first elongated resilient and elastic members are 5 to 30 rubber threads that are made of synthetic rubber, 155 to 1,880 dtex in fineness and 200 to 350% in extension ratio, and are arranged at intervals of 1 to 15 mm, the second elongated resilient and elastic members are 2 to 10 rubber threads that are made of synthetic rubber, 155 to 1,880 dtex in fineness and 150 to 300% in extension ratio, and are arranged at intervals of 5 to 40 mm, the third elongated resilient and elastic members are 4 to 30 rubber threads that are made of synthetic rubber, 155 to 1,880 dtex in fineness and 150 to 300% in extension ratio, and are arranged at intervals of 3 to 8 mm, a length of the upper end portion of the back-side main unit section and a length of the upper end portion of the ventral-side main unit section are equal and 15 to 80 mm in the up-down direction, and the back-side waist elongated resilient and elastic members and the ventral-side elongated resilient and elastic members are each 3 to 22 rubber threads that are made of synthetic rubber, 155 to 1,880 dtex in fineness and 150 to 400% in extension ratio, and are arranged at intervals of 4 to 12 mm.

* * * * *